US012806360B2

(12) United States Patent
Collins et al.

(10) Patent No.: US 12,806,360 B2
(45) Date of Patent: Nov. 24, 2026

(54) RESPIRATORY INTERFACE ASSEMBLY

(71) Applicant: Fisher & Paykel Healthcare Limited, Auckland (NZ)

(72) Inventors: Janine Elizabeth Collins, Auckland (NZ); Blair Raymund Dadson Murphy, Auckland (NZ); Lydia Kathleen Mcglashan, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 935 days.

(21) Appl. No.: 17/774,282

(22) PCT Filed: Nov. 13, 2020

(86) PCT No.: PCT/NZ2020/050151

§ 371 (c)(1),
(2) Date: May 4, 2022

(87) PCT Pub. No.: WO2021/096371

PCT Pub. Date: May 20, 2021

(65) Prior Publication Data

US 2022/0401685 A1 Dec. 22, 2022

Related U.S. Application Data

(60) Provisional application No. 62/936,155, filed on Nov. 15, 2019.

(51) Int. Cl.
*A61M 16/06* (2006.01)

(52) U.S. Cl.
CPC ..... *A61M 16/0683* (2013.01); *A61M 2205/02* (2013.01)

(58) Field of Classification Search
CPC ......................... A61M 16/0683; A62B 18/084
See application file for complete search history.

(56) References Cited

U.S. PATENT DOCUMENTS

| | | | | |
|---|---|---|---|---|
| 3,388,705 | A * | 6/1968 | Grosshandler .... | A61M 16/0463 128/207.14 |
| 4,852,564 | A * | 8/1989 | Sheridan .............. | A61M 16/08 138/119 |

(Continued)

FOREIGN PATENT DOCUMENTS

| | | |
|---|---|---|
| EP | 3429668 A2 | 1/2019 |
| JP | 2016-509953 | 4/2016 |

(Continued)

OTHER PUBLICATIONS

International Search Report and Written Opinion in PCT/NZ2020/050151, dated Feb. 23, 2021.

*Primary Examiner* — Bradley H Philips
(74) *Attorney, Agent, or Firm* — VIA LLP

(57) ABSTRACT

A respiratory interface assembly includes a patient interface, such as a nasal mask, and a headgear arrangement. The headgear arrangement can have one or more semi-rigid straps, which can be a composite construction of an outer fabric and a plastic core. The outer fabric can be knitted. The headgear arrangement can include a composite rear portion having an upper strap and lower strap, which are configured to be adjustable relative to one another.

23 Claims, 29 Drawing Sheets

(56) References Cited

U.S. PATENT DOCUMENTS

| | | | | |
|---|---|---|---|---|
| 5,269,026 | A * | 12/1993 | McManus | A42B 1/08 2/418 |
| 5,724,677 | A * | 3/1998 | Bryant | A41D 13/1146 2/206 |
| 7,296,575 | B1 * | 11/2007 | Radney | A61M 16/06 128/207.11 |
| 8,118,026 | B2 * | 2/2012 | Gebrewold | A62B 23/025 128/206.16 |
| 8,950,404 | B2 * | 2/2015 | Formica | B32B 27/065 2/209.3 |
| 10,874,814 | B2 * | 12/2020 | Huddart | A61M 16/0666 |
| 11,458,271 | B2 * | 10/2022 | Dunn | B29C 66/729 |
| 2006/0090760 | A1 | 5/2006 | Gradon et al. | |
| 2009/0044808 | A1 * | 2/2009 | Guney | A61M 16/0605 128/207.18 |
| 2010/0224199 | A1 * | 9/2010 | Smith | A61M 16/06 128/863 |
| 2011/0220113 | A1 | 9/2011 | Newman et al. | |
| 2015/0290415 | A1 | 10/2015 | Dunn | |
| 2016/0030696 | A1 | 2/2016 | Klenner et al. | |
| 2016/0074614 | A1 * | 3/2016 | Huddart | A61M 16/208 128/204.18 |
| 2017/0015701 | A1 | 1/2017 | Cox et al. | |
| 2018/0207385 | A1 * | 7/2018 | Freestone | A61M 16/0605 |
| 2018/0236276 | A1 * | 8/2018 | Moon | A44B 11/006 |
| 2018/0318541 | A1 | 11/2018 | Walls et al. | |
| 2019/0151592 | A1 | 5/2019 | Bornholdt et al. | |
| 2022/0126049 | A1 * | 4/2022 | Amarasinghe | A61M 16/0875 |

FOREIGN PATENT DOCUMENTS

| | | | | |
|---|---|---|---|---|
| JP | 2019-509161 | | 4/2019 | |
| WO | WO 2013/026092 | A1 | 2/2013 | |
| WO | WO 2013/071359 | A1 | 5/2013 | |
| WO | WO 2014/077708 | A1 | 5/2014 | |
| WO | WO 2016/043603 | A1 | 3/2016 | |
| WO | WO 2017/031263 | A1 | 2/2017 | |
| WO | WO 2017/158474 | A2 | 9/2017 | |
| WO | WO-2017160166 | A1 * | 9/2017 | A61M 16/0616 |

* cited by examiner

RESPIRATORY INTERFACE ASSEMBLY

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND

Field

The present disclosure relates to a respiratory interface assembly. In particular, the present disclosure relates to a headgear of a respiratory interface assembly.

Description of Related Art

In assisted breathing, respiratory gases are supplied to a patient through a patient interface via one or more flexible breathing tubes. The patient interface can be a nasal cannula, nasal mask, full face or oro-nasal mask, endotracheal tube, or other known types of interfaces. The patient interface is held in place on the head of the user by a headgear arrangement.

In the specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

SUMMARY

The systems, methods and devices described herein have innovative aspects, no single one of which is indispensable or solely responsible for their desirable attributes. Without limiting the scope of the claims, some of the advantageous features will now be summarized.

An aspect of the present disclosure involves a rear portion of a respiratory mask headgear, which includes a unitary body portion comprising a plastic material. The body portion includes an upper strap having a first end, a second end, a length between the first end and the second end, and a width. The body portion also includes a lower strap having a first end, a second end, a length between the first end and the second end, and a width. The body portion includes a junction between the first end of the upper strap and the first end of the lower strap. The junction comprises a base portion and a transition region between the base portion and one of the upper strap and the lower strap. The base portion defines a width. A width of the transition region is less than the width of the base portion of the junction and the width of the respective upper strap or lower strap to which the transition region is joined.

In some configurations, the width of the transition region is less than about one-half of the width of the respective upper strap or lower strap to which the transition region is joined.

In some configurations, the width of the transition region is less than about one-third of the width of the respective upper strap or lower strap to which the transition region is joined.

In some configurations, the transition region defines a length that is less than the width of the base portion of the junction and/or the width of the respective upper strap or lower strap to which the transition region is joined.

In some configurations, the length of the transition region is less than about two-thirds or one-half of the width of the respective upper strap or lower strap to which the transition region is joined.

In some configurations, the transition region is defined by a slot having a maximum width that is less than the width of the base portion of the junction and/or the width of the respective upper strap or lower strap adjacent the slot.

In some configurations, the junction is symmetrical about an axis passing through the junction and between the upper strap and the lower strap.

In some configurations, each of the upper strap and the lower strap comprise a main strap portion having a first thickness and at least one flange portion having a second thickness that is smaller than the first thickness, wherein the main strap portion extends along an entirety of the length of the strap, and wherein the at least one flange portion extends along a substantial portion of the length of the strap.

In some configurations, the at least one flange portion extends along only a portion of the length of the strap.

In some configurations, the main strap portion or the main strap portion and the flange define an entirety of the width of the strap at any location along the length of the strap.

In some configurations, the main strap portion defines an entirety of one of the upper edge and the lower edge of the strap.

In some configurations, the main strap portion defines an entire width of a central portion of the strap.

In some configurations, the at least one flange portion comprises a first flange portion and a second flange portion located on opposing sides of the central portion of the strap.

In some configurations, each of the first flange portion and the second flange portion extend along a substantial entirety of a respective side of the user's head in use.

In some configurations, the length of the upper strap is a first length and the length of the lower strap is a second length, wherein the second length is greater than the first length.

In some configurations, the width of the lower strap is greater than the width of the upper strap.

In some configurations, the central portion of the upper strap defines a length that is less than a length of the central portion of the lower strap.

In some configurations, the transition region is a first transition region and the junction further comprises a second transition region, the first transition region located between the base portion and the upper strap and the second transition region located between the base portion and the lower strap.

In some configurations, a width of the second transition region is greater than a width of the first transition region.

In some configurations, the body portion comprises a fabric inner layer, a fabric outer layer and an interior plastic layer permanently joined as an integral structure as a result of the interior plastic layer being introduced into a space between the fabric inner layer and the fabric outer layer in a molten state and allowed to harden.

In some configurations, the fabric inner layer and the fabric outer layer are knitted.

In some configurations, the fabric inner layer and the fabric outer layer are joined to form an edge fabric layer along the upper edge and the lower edge of the upper strap and the lower strap.

In some configurations, a thickness of the edge fabric layer along the upper edge and the lower edge of the upper strap and the lower strap is greater than a thickness of the fabric inner layer and the fabric outer layer.

In some configurations, the rear portion further comprises at least one fabric layer configured to enclose an interior plastic layer. The at least one fabric layer can comprise at least one width. The at least one width can comprises a transition region width positioned adjacent the transition region.

In some configurations, the at least one fabric layer can comprise at least one upper strap fabric layer and at least one lower strap fabric layer.

In some configurations, the at least one width can comprise an upper strap width of the at least one upper strap fabric layer and a lower strap width of the at least one lower strap fabric layer.

In some configurations, the at least one fabric layer can comprise the upper strap width along the upper strap and the lower strap width along the lower strap.

In some configurations, the transition region width can be the same as or similar to the upper strap width.

In some configurations, the transition region width can be the same as or similar to the lower strap width.

In some configurations, the lower strap width can be greater than the upper strap width.

In some configurations, the transition region width of the at least one fabric layer can be greater than the width of the transition region of the junction.

In some configurations, the at least one fabric layer can comprise at least one fabric flap adjacent the transition region. The width of the at least one fabric flap can be greatest where the width of the transition region is the smallest.

In some configurations, the junction between the first end of the upper strap and the first end of the lower strap is a first junction, further comprising a second junction between the second end of the upper strap and the second end of the lower strap, the second junction comprising a transition region between the base portion and one or both of the upper strap and the lower strap.

An aspect of the present disclosure involves a respiratory mask headgear including any of the rear portions as described above and a pair of side straps. Each of the side straps extend from a respective one of the first junction and the second junction. Each of the side straps includes an elongate plastic member coupled to the plastic material of the body portion of the rear portion.

In some configurations, the elongate plastic member of each of the side straps is coupled to the plastic material of the body portion by an overmolded connection.

In some configurations, each of the side straps comprises a hub at an end of the elongate plastic member, wherein the hub comprises a port configured to receive the molten plastic material that forms the body portion of the rear portion.

In some configurations, the hub further comprises a flow channel connected to the port, the flow channel configured to permit the molten plastic material to exit the hub and flow into the space between the inner fabric layer and the outer fabric layer.

In some configurations, each of the side straps further comprises a fabric inner layer and a fabric outer layer connected to the fabric inner layer and the fabric outer layer of the rear portion.

In some configurations, the fabric inner layer and the fabric outer layer of the side straps are relatively elastic and the fabric inner layer and the fabric outer layer of the rear portion are relatively inelastic.

In some configurations, the fabric inner layer and the fabric outer layer of the side straps are formed as a single knitted structure with the fabric inner layer and the fabric outer layer of the rear portion.

An aspect of the present disclosure involves a respiratory mask assembly including any one of the headgear described above, a respiratory mask, and a first directional lock and a second directional lock coupled to the respiratory mask. The elongate plastic member of each of the side straps comprises a filament portion, wherein the filament portion of each of the side straps passes through a respective one of the first and second directional locks, each of the first and second directional locks are configured to provide a first resistance force to movement of the filament portion in a first direction tending to lengthen the side strap and a second resistance force to movement of the filament portion in a second direction tending to shorten the side strap, wherein the first resistance force is greater than the second resistance force.

In some configurations, the first resistance force is configured to prevent movement of the filament portion in the first direction in response to a blow-off force generated by the respiratory mask.

In some configurations, the second resistance force is smaller than an elastic force of the inner fabric layer and the outer fabric layer of the side straps such that the elastic force can move the filament portion in the second direction to shorten the side straps.

In some configurations, the respiratory mask is a nasal mask.

An aspect of the present disclosure involves a rear portion of a respiratory mask headgear including a unitary body portion comprising a plastic material. The body portion includes an upper strap having a first end, a second end, a length between the first end and the second end, and a width. The body portion also includes a lower strap having a first end, a second end, a length between the first end and the second end, and a width. The body portion includes a junction between the first end of the upper strap and the first end of the lower strap, the junction comprising a base portion and a living hinge between the base portion and one of the upper strap and the lower strap.

In some configurations, the living hinge defines a length that is less than a width of the base portion of the junction and/or the width of the respective upper strap or lower strap to which the living hinge is joined.

In some configurations, the length of the living hinge is less than about two-thirds or one-half of the width of the respective upper strap or lower strap to which the living hinge is joined.

In some configurations, the living hinge is defined by a slot.

In some configurations, the junction is symmetrical about an axis passing through the junction and between the upper strap and the lower strap.

In some configurations, each of the upper strap and the lower strap comprise a main strap portion having a first thickness and at least one flange portion having a second thickness that is smaller than the first thickness, wherein the main strap portion extends along an entirety of the length of the strap from the first junction to the second junction, and wherein the at least one flange portion extends along a substantial portion of the length of the strap.

In some configurations, the at least one flange portion extends along only a portion of the length of the strap.

In some configurations, the main strap portion or the main strap portion and the flange define an entirety of the width of the strap at any location along the length of the strap.

In some configurations, the main strap portion defines an entirety of one of the upper edge and the lower edge of the strap.

In some configurations, the main strap portion defines an entire width of a central portion of the strap.

In some configurations, the at least one flange portion comprises a first flange portion and a second flange portion located on opposing sides of the central portion of the strap.

In some configurations, each of the first flange portion and the second flange portion extend along a substantial entirety of a respective side of the user's head in use.

In some configurations, the length of the upper strap is a first length and the length of the lower strap is a second length, wherein the second length is greater than the first length.

In some configurations, the width of the lower strap is greater than the width of the upper strap.

In some configurations, the central portion of the upper strap defines a length that is less than a length of the central portion of the lower strap.

In some configurations, the living hinge is a first living hinge and the junction further comprises a second living hinge, the first living hinge located between the base portion and the upper strap and the second living hinge located between the base portion and the lower strap.

In some configurations, the body portion comprises a fabric inner layer, a fabric outer layer and an interior plastic layer permanently joined as an integral structure as a result of the interior plastic layer being introduced into a space between the fabric inner layer and the fabric outer layer in a molten state and allowed to harden.

In some configurations, the fabric inner layer and the fabric outer layer are knitted.

In some configurations, the fabric inner layer and the fabric outer layer are joined to form an edge fabric layer along the upper edge and the lower edge of the upper strap and the lower strap.

In some configurations, a thickness of the edge fabric layer along the upper edge and the lower edge of the upper strap and the lower strap is greater than a thickness of the fabric inner layer and the fabric outer layer.

In some configurations, the junction between the first end of the upper strap and the first end of the lower strap is a first junction, further comprising a second junction between the second end of the upper strap and the second end of the lower strap, the second junction comprising a living hinge between the base portion and one or both of the upper strap and the lower strap.

An aspect of the present disclosure involves a respiratory mask headgear including any one of the rear portions described above and a pair of side straps. Each of the side straps extend from a respective one of the first junction and the second junction. Each of the side straps includes an elongate plastic member coupled to the plastic material of the body portion of the rear portion.

In some configurations, the elongate plastic member of each of the side straps is coupled to the plastic material of the body portion by an overmolded connection.

In some configurations, each of the side straps comprises a hub at an end of the elongate plastic member, wherein the hub comprises a port configured to receive the molten plastic material that forms the body portion of the rear portion.

In some configurations, the hub further comprises a flow channel connected to the port, the flow channel configured to permit the molten plastic material to exit the hub and flow into the space between the inner fabric layer and the outer fabric layer.

In some configurations, each of the side straps further comprises a fabric inner layer and a fabric outer layer connected to the fabric inner layer and the fabric outer layer of the rear portion.

In some configurations, the fabric inner layer and the fabric outer layer of the side straps are relatively elastic and the fabric inner layer and the fabric outer layer of the rear portion are relatively inelastic.

In some configurations, the fabric inner layer and the fabric outer layer of the side straps are formed as a single knitted structure with the fabric inner layer and the fabric outer layer of the rear portion.

An aspect of the present disclosure involves a respiratory mask assembly including any of the headgear described above, a respiratory mask, and a first directional lock and a second directional lock coupled to the respiratory mask. The elongate plastic member of each of the side straps includes a filament portion, wherein the filament portion of each of the side straps passes through a respective one of the first and second directional locks, each of the first and second directional locks configured to provide a first resistance force to movement of the filament portion in a first direction tending to lengthen the side strap and a second resistance force to movement of the filament portion in a second direction tending to shorten the side strap, wherein the first resistance force is greater than the second resistance force.

In some configurations, the first resistance force is configured to prevent movement of the filament portion in the first direction in response to a blow-off force generated by the respiratory mask.

In some configurations, the second resistance force is smaller than an elastic force of the inner fabric layer and the outer fabric layer of the side straps such that the elastic force can move the filament portion in the second direction to shorten the side straps.

In some configurations, the respiratory mask is a nasal mask.

An aspect of the present disclosure involves a rear portion of a respiratory mask headgear including an upper strap having a first end, a second end, and a first length between the first end and the second end. The rear portion also includes a lower strap having a first end, a second end, and a second length between the first end and the second end. The first end of the upper strap is connected to the first end of the lower strap and wherein the second end of the upper strap is connected to the second end of the lower strap. The second length is greater than the first length.

An aspect of the present disclosure involves a rear portion of a respiratory mask headgear including a unitary body portion comprising a plastic material. The body portion includes an upper strap having a lower edge, a first end, a second end, a length between the first end and the second end, and a width. The body portion also includes a lower strap having an upper edge, a first end, a second end, a length between the first end and the second end, and a width. A separation distance is defined between the lower edge of the upper strap and the upper edge of the lower strap. A junction is located between an end of the upper strap and an end of the lower strap. The junction comprises a base portion and a flex region between the base portion and one of the upper strap and the lower strap. The flex region is configured to permit the respective upper strap or lower strap to which the flex region is joined to pivot relative to the base portion of the junction to increase the separation distance.

In some configurations, the junction is configured to permit the separation distance to be increased until an angle of at least about 90 degrees is formed between the upper strap and the lower strap.

In some configurations, the junction is configured to permit the separation distance to be increased until an angle of at least about 135 degrees is formed between the upper strap and the lower strap.

In some configurations, the width of the flex region is less than about one-half of the width of the respective upper strap or lower strap to which the flex region is joined.

In some configurations, the width of the flex region is less than about one-third of the width of the respective upper strap or lower strap to which the flex region is joined.

In some configurations, the flex region defines a length that is less than the width of the base portion of the junction and/or the width of the respective upper strap or lower strap to which the flex region is joined.

In some configurations, the length of the flex region is less than about two-thirds or one-half of the width of the respective upper strap or lower strap to which the flex region is joined.

In some configurations, the flex region is defined by a slot having a maximum width that is less than the width of the base portion of the junction and/or the width of the respective upper strap or lower strap adjacent the slot.

In some configurations, the junction is symmetrical about an axis passing through the junction and between the upper strap and the lower strap.

In some configurations, each of the upper strap and the lower strap comprise a main strap portion having a first thickness and at least one flange portion having a second thickness that is smaller than the first thickness, wherein the main strap portion extends along an entirety of the length of the strap, and wherein the at least one flange portion extends along a substantial portion of the length of the strap.

In some configurations, the at least one flange portion extends along only a portion of the length of the strap.

In some configurations, the main strap portion or the main strap portion and the flange define an entirety of the width of the strap at any location along the length of the strap.

In some configurations, the main strap portion defines an entirety of one of the upper edge and the lower edge of the strap.

In some configurations, the main strap portion defines an entire width of a central portion of the strap.

In some configurations, the at least one flange portion comprises a first flange portion and a second flange portion located on opposing sides of the central portion of the strap.

In some configurations, each of the first flange portion and the second flange portion extend along a substantial entirety of a respective side of the user's head in use.

In some configurations, the length of the upper strap is a first length and the length of the lower strap is a second length, wherein the second length is greater than the first length.

In some configurations, the width of the lower strap is greater than the width of the upper strap.

In some configurations, the central portion of the upper strap defines a length that is less than a length of the central portion of the lower strap.

In some configurations, the flex region is a first flex region and the junction further comprises a second flex region, the first flex region located between the base portion and the upper strap and the second flex region located between the base portion and the lower strap.

In some configurations, the body portion comprises a fabric inner layer, a fabric outer layer and an interior plastic layer permanently joined as an integral structure as a result of the interior plastic layer being introduced into a space between the fabric inner layer and the fabric outer layer in a molten state and allowed to harden.

In some configurations, the fabric inner layer and the fabric outer layer are knitted.

In some configurations, the fabric inner layer and the fabric outer layer are joined to form an edge fabric layer along the upper edge and the lower edge of the upper strap and the lower strap.

In some configurations, a thickness of the edge fabric layer along the upper edge and the lower edge of the upper strap and the lower strap is greater than a thickness of the fabric inner layer and the fabric outer layer.

In some configurations, the junction between the first end of the upper strap and the first end of the lower strap is a first junction, and the rear portion further includes a second junction between the second end of the upper strap and the second end of the lower strap. The second junction comprises a flex region between the base portion and one or both of the upper strap and the lower strap.

An aspect of the present disclosure involves a respiratory mask headgear including any of the rear portions described above and a pair of side straps, each of the side straps extending from a respective one of the first junction and the second junction, wherein each of the side straps comprises an elongate plastic member coupled to the plastic material of the body portion of the rear portion.

In some configurations, the elongate plastic member of each of the side straps is coupled to the plastic material of the body portion by an overmolded connection.

In some configurations, each of the side straps comprises a hub at an end of the elongate plastic member, wherein the hub comprises a port configured to receive the molten plastic material that forms the body portion of the rear portion.

In some configurations, the hub further comprises a flow channel connected to the port, the flow channel configured to permit the molten plastic material to exit the hub and flow into the space between the inner fabric layer and the outer fabric layer.

In some configurations, each of the side straps further comprises a fabric inner layer and a fabric outer layer connected to the fabric inner layer and the fabric outer layer of the rear portion.

In some configurations, the fabric inner layer and the fabric outer layer of the side straps are relatively elastic and the fabric inner layer and the fabric outer layer of the rear portion are relatively inelastic.

In some configurations, the fabric inner layer and the fabric outer layer of the side straps are formed as a single knitted structure with the fabric inner layer and the fabric outer layer of the rear portion.

An aspect of the present disclosure involves a respiratory mask assembly having any of the headgear described above, a respiratory mask, and a first directional lock and a second directional lock coupled to the respiratory mask. The elongate plastic member of each of the side straps includes a filament portion. The filament portion of each of the side straps passes through a respective one of the first and second directional locks. Each of the first and second directional locks is configured to provide a first resistance force to movement of the filament portion in a first direction tending to lengthen the side strap and a second resistance force to movement of the filament portion in a second direction tending to shorten the side strap. The first resistance force is greater than the second resistance force.

In some configurations, the first resistance force is configured to prevent movement of the filament portion in the first direction in response to a blow-off force generated by the respiratory mask.

In some configurations, the second resistance force is smaller than an elastic force of the inner fabric layer and the outer fabric layer of the side straps such that the elastic force can move the filament portion in the second direction to shorten the side straps.

In some configurations, the respiratory mask is a nasal mask.

An aspect of the present disclosure involves a rear portion of a respiratory mask headgear including a unitary body portion comprising a plastic material. The body portion includes an upper strap having a first end, a second end, a length between the first end and the second end, and a width. The body portion also includes a lower strap having a first end, a second end, a length between the first end and the second end, and a width. The body portion includes a first junction and a second junction. The first junction is located between the first end of the upper strap and the first end of the lower strap and the second junction is located between the second end of the upper strap and the second end of the lower strap. Each of the upper strap and the lower strap includes a main strap portion having a first thickness and at least one flange portion having a second thickness that is smaller than the first thickness. The main strap portion extends along an entirety of the length of the strap from the first junction to the second junction. The at least one flange portion extends along a substantial portion of the length of the strap.

In some configurations, the at least one flange portion extends along only a portion of the length of the strap.

In some configurations, the main strap portion or the main strap portion and the flange define an entire width of the strap at any location along the length of the strap.

In some configurations, the main strap portion defines an entirety of one of an upper edge and a lower edge of the strap.

In some configurations, the main strap portion defines an entire width of a central portion of the strap.

In some configurations, the at least one flange portion comprises a first flange portion and a second flange portion located on opposing sides of the central portion of the strap.

In some configurations, each of the first flange portion and the second flange portion extend along a substantial entirety of a respective side of the user's head in use.

In some configurations, the length of the upper strap is a first length and the length of the lower strap is a second length, wherein the second length is greater than the first length.

In some configurations, each of the first junction and the second junction comprises a base portion and a flex region between the base portion and one or both of the upper strap and the lower strap, wherein the flex region is configured to permit the respective upper strap or lower strap to which the flex region is joined to pivot relative to the base portion to increase a separation distance between a lower edge of the upper strap and an upper edge of the lower strap.

In some configurations, the base portion defines a width, the flex region comprises a transition region defining a width that is less than the width of the base portion of the junction and the width of the respective upper strap or lower strap to which the flex region is joined.

In some configurations, the flex region comprises a living hinge.

An aspect of the present disclosure involves a pair of side straps of a respiratory mask headgear, which each can include an elongate plastic member and a support housing. The elongate plastic member can include a first portion, a second portion, a hub, and a transition portion. The first portion can include a first end and a second end. The second end can include a mechanical stop extending radially outward from the elongate plastic member. The mechanical stop can define an extension hard stop. A width of the second can be less than a width of the first portion. The hub can include a first end opposite a second end. The second end of the hub can include an abutment surface that can define a retraction hard stop. The second end of the hub can be adjacent the first end of the first portion. The transition portion can be positioned between the second end of the first portion and the second portion. The support housing can be configured to restrain at least a portion of the elongate plastic member. The support housing can define an interior channel configured to receive the elongate plastic member. The support housing can include a lateral collar, a medial collar, and a middle portion between the lateral collar and the medial collar.

In some configurations, a lateral wall of the lateral collar can define a first abutment surface of the lateral collar configured to abut the abutment surface of the hub and a medial wall of the lateral collar can define a second abutment surface configured to abut the mechanical stop.

In some configurations, each of the side straps can further include at least one length that can include a maximum length and a minimum length.

In some configurations, the pair of side straps can include the minimum length when the first abutment surface of the lateral collar abuts the abutment surface of the hub.

In some configurations, the pair of side straps can include the maximum length when the second abutment surface of the lateral collar abuts the mechanical stop.

In some configurations, the hub can include a substantially rectangular shape and a length of the hub can be greater than a width of the hub.

In some configurations, the hub can include a first side opposite a second side. A length of the first side can be greater than a length of the second side. A width of the first side can be greater than a width of the second side.

In some configurations, the width of the first side of the hub can be measured between a first side of the first portion and a first outer edge of the first side of the hub. The width of the second side can be measured between a second side of the first portion and a second outer edge of the second side of the hub.

In some configurations, the hub and the first portion can include respective exterior surfaces and interior surfaces.

In some configurations, the exterior surface of the first portion can be continuous with the exterior surface of the hub.

In some configurations, the hub can include a hub thickness and the first portion can include a first thickness. The hub thickness can be greater than the first thickness. The hub thickness can be measured between the exterior and interior surfaces of the hub. The first thickness can be measured between the exterior and interior surfaces of the first portion.

In some configurations, the interior surface of the hub can be offset from the interior surface of the first portion.

In some configurations, the offset between the interior surfaces of the hub and the first portion can define the abutment surface of the hub.

An aspect of the present disclosure involves a respiratory mask headgear including any of the pairs of straps as described above and a rear portion. The rear portion can include a unitary body portion including a plastic material. The unitary body portion can include an upper strap, a lower strap, a first junction, and a second junction. The upper strap can have a first end, a second end, a length between the first end and the second end, and a width. The lower strap can have a first end, a second end, a length between the first end and the second end, and a width. The first junction can be positioned between the first end of the upper strap and the first end of the lower strap. The second junction can be positioned between the second end of the upper strap and the second end of the lower strap. Each of the side straps can extend from a respective one of the first junction and the second junction. The first end of the hub of each of the side straps can be overmolded to the respective one of the first junction and the second junction. The second end of the hub of each of the side straps can remain uncovered.

An aspect of the present disclosure involves a pair of side straps of a respiratory mask headgear, which can each include an elongate plastic member. The elongate plastic member including a first portion, a second portion, and a hub. The first portion can include a first end, a second end, an interior surface, an exterior surface, and a first portion thickness measured between the interior and exterior surfaces of the first portion. A width of the second portion can be less than a width of the first portion. The hub can include a first end opposite a second end, a first side opposite a second side, an interior surface, an exterior surface continuous with the exterior surface of the first portion, and a hub thickness measured between the interior and exterior surfaces of the hub. The hub thickness can be greater than the first portion thickness. The second end of the hub can be adjacent the first end of the first portion and include an abutment surface that can define a retraction hard stop. The first and second sides of the hub can extend between the first and second ends of the hub and can be separated by a longitudinal axis of the first portion. A first length of the first side of the hub can be greater than a second length of the second side of the hub. A first width of the first side of the hub can be greater than a second width of the second side of the hub.

In some configurations, the first width of the first side of the hub can be measured between the longitudinal axis of the first portion and a first outer edge of the first side of the hub. The first outer edge of the hub can be substantially parallel to the longitudinal axis of the first portion.

In some configurations, the second width of the second side of the hub can be measured between the longitudinal axis of the first portion and a second outer edge of the second side of the hub. The second outer edge of the hub can be substantially parallel to the longitudinal axis of the first portion.

In some configurations, the first length of the first side of the hub can be measured between the first and second ends of the hub.

In some configurations, the second length of the second side of the hub can be measured between the first and second ends of the hub.

In some configurations, the first end of the first side of the hub can be continuous with the first end of the second side of the hub.

In some configurations, the second end of the first side of the hub can be offset from the second end of the second side of the hub.

In some configurations, the offset between the second end of the first side of the hub and the second end of the second side of the hub can define an orientation notch.

In some configurations, the interior surface of the hub can be offset from the interior surface of the first portion.

In some configurations, the offset between the interior surface of the hub and the interior surface of the first portion can define the abutment surface of the hub. The abutment surface can be located on the second end of the hub.

In some configurations, the second end of the first portion can include a mechanical stop extending radially outward from the exterior surface of the first portion. The mechanical stop can define an extension hard stop.

In some configurations, the mechanical stop can include a tooth edge and a ramped surface.

In some configurations, each of the side straps can include a support housing configured to restrain at least a portion of the elongate plastic member. The support housing can define an interior channel configured to receive the elongate plastic member. The support housing can include a lateral collar, a medial collar, and a middle portion between the later collar and the medial collar.

In some configurations, the support housing can include an interior side and an exterior side. The exterior side of the middle portion of the support housing can include an elongate opening. The interior side of the support housing can include a continuous wall.

In some configurations, the lateral collar can be configured to abut with the abutment surface of the hub.

In some configurations, the lateral collar can be configured to abut with the mechanical stop of the elongate plastic member.

An aspect of the present disclosure involves a rear portion of a respiratory mask headgear that can be formed from a unitary structure of molten plastic molded in a three-dimensional shape. The unitary structure of molten plastic can include a unitary molded upper strap and a unitary molded lower strap. The unitary molded upper strap can have a first end, a second end, and a first length between the first end and the second end. The unitary molded upper strap can include a first curvature configured to approximate or conform to the shape of an upper portion of a user's head. The unitary molded lower strap can have a first end, a second end, and a second length between the first end and the second end. The unitary molded lower strap can include a second curvature configured to approximate or conform to the shape of a lower or rear portion of the user's head. The first end of the upper strap can form a first junction with the first end of the lower strap and the second end of the upper strap can form a second junction with the second end of the lower strap.

In some configurations, the second length can be greater than the first length.

In some configurations, the rear portion can include a molded composite structure. The molded composite structure can have at least one fabric layer and at least one plastic layer permanently connected to one another.

In some configurations, a user-contacting surface of the rear portion can include a flush surface. The flush surface can have little to no variation in thickness.

In some configurations, the first junction and/or the second junction can include a base portion and a flex region. The flex region can be positioned between the base portion and one of the upper strap and the lower strap.

In some configurations, the upper strap and/or the lower strap can include a relatively stiffer or reinforced portion having a greater thickness than adjacent portions of the upper and/or lower strap.

In some configurations, the upper strap and/or the lower strap can include one or more relatively less stiff portions having a lesser thickness than adjacent portions of the upper and/or lower strap.

In some configurations, the first and/or second junction is/are formed with an initial angle of between about 60-100 degrees, about 70-90 degrees, or about 75-80 degrees.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

DETAILED DESCRIPTION

Figure 1:
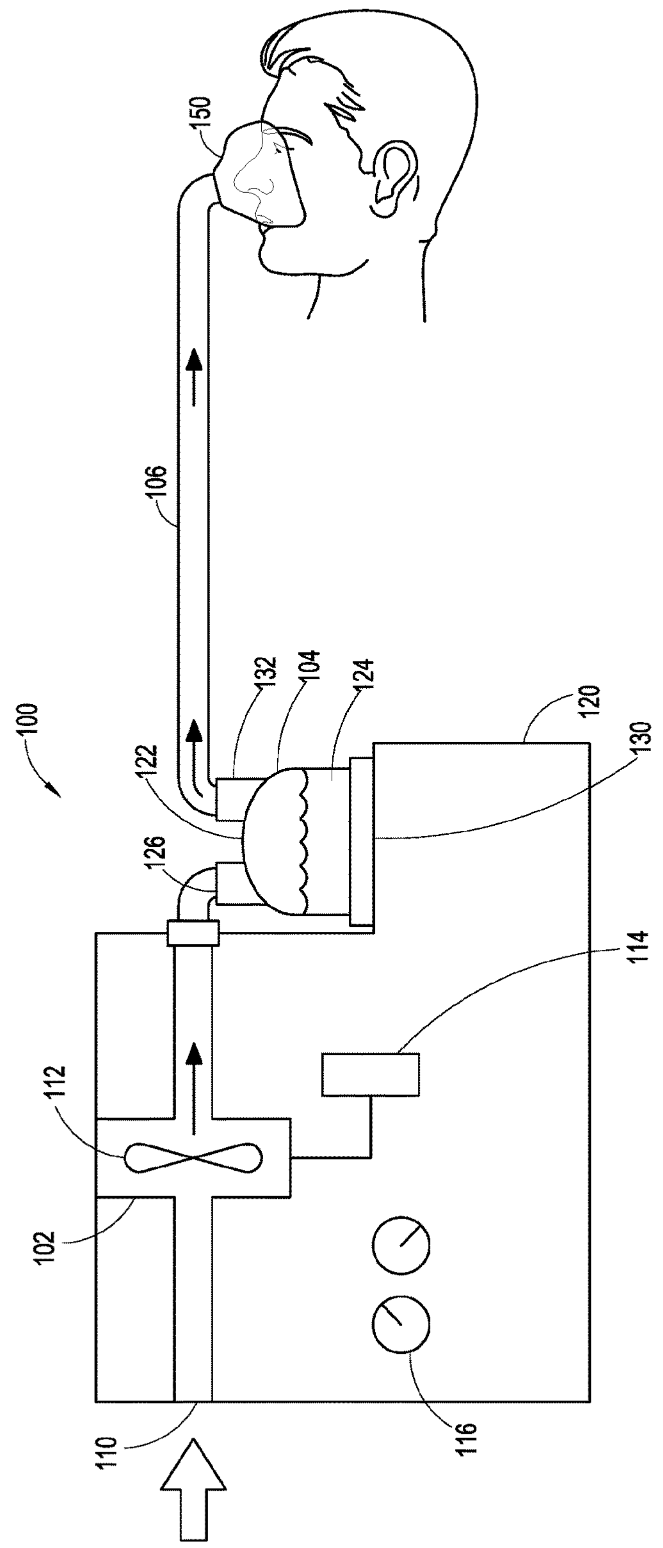
FIG. 1 is a schematic representation of a respiratory system configured to supply pressurized and humidified breathing gases to a user through a patient interface.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extend beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as “first,” “second,” “third,” and so on may be used to describe separate components. Such terminology may include the words specifically mentioned above, derivatives thereof, and words of similar import.

System Overview

FIG. 1 illustrates an example respiratory therapy system suitable for supplying breathing gases to a user for positive airway pressure (PAP) therapy (e.g., continuous positive airway pressure (CPAP) therapy) or non-invasive ventilation (NW) therapy. The example respiratory therapy system 100 may include a gas source 102, a humidifier 104, a patient interface assembly 150 and a breathing gas circuit 106 that connects the humidifier 104 (or gas source 102) to the patient interface assembly 150. The gas source 102 can provide a supply of breathing gas to the humidifier 104. The gas source 102 may comprise a blower in which breathing gas, e.g., ambient air, is drawn into the gas source 102 through an inlet 110 in the gas source casing by an impeller 112. The rotational speed of the impeller 112 may be modulated to regulate the quantity of air drawn into the gas source 102 and the supply of breathing gas delivered to the respiratory therapy system 100. Breathing gas may include any single gas or multiple gases that are breathable by a user of the system 100.

The pressure and/or flow rate of breathing gas exiting the gas source 102 may be regulated by a controller 114. The controller 114 may modulate the rotational speed of the impeller 112 according to one or more predetermined algorithms and in accordance with one or more user inputs that may be provided via a user input 116.

The illustrated gas source 102 is an actively controlled flow generator. Other gas sources, such as a compressed air cylinder with suitable pressure or flow regulation, may also be used to supply breathing gas. The outlet of the gas source 102 may be coupled to a separate humidifier 104. The humidifier 104 may be configured to heat and/or humidify the breathing gas prior to delivery, e.g., delivery to the user. In some embodiments, the humidifier is integrated with the gas supply. The humidifier 104 may include a base 120 and a humidifier chamber 122. The chamber 122 may be configured to hold humidification fluid 124, such as water, and may be disengaged, e.g., temporarily disengaged or permanently disengaged, from the humidifier base 120 to allow it to be filled or replaced. The humidifier 104 receives gases from the gas source 102 through chamber inlet 126. The humidifier base 120 can include a heater such as a heater plate 130. The chamber 122 rests on the heater plate 130 when engaged with the humidifier base 120. The heater plate 130 dissipates heat, e.g., heat generated by electrical resistance, to the chamber 122. The chamber 122 preferably has a heat conductive base to enable the heat generated by the heater plate 130 to pass efficiently to the humidification fluid 124. The controller 114 can also control the humidifier 104, and in particular the supply of electrical energy to the heater plate 130, to regulate any function of the humidifier 104, e.g., the temperature and humidity of the breathing gas supplied to the user.

The breathing gas can be supplied to the user via a chamber outlet 132 and the breathing gas circuit 106 in the form of a conduit, which may incorporate a heating or warming element, e.g., a heater wire, to heat or warm (e.g., keep hot or warm) the breathing gases during transportation to the patient interface assembly 150. The electrical energy supplied to the heater wire may be controlled by the controller 114. The controller 114 may receive feedback from one or more sensors incorporated in a control network throughout the respiratory therapy system to monitor properties of the breathing gas, such as, but not limited to, pressure, flow, temperature, and/or humidity.

The patient interface assembly 150 couples the user with the respiratory therapy system 100, such that gases, e.g., heated and humidified gases from the humidifier 104, may be delivered to the user’s respiratory system. Breathing gases can be delivered to the user at, or near, optimal temperature and humidity (e.g., warmed and fully saturated with water vapor at temperatures of between 27 and 37° C.) as the gases are delivered to the user’s nares and or mouth. Emulating the conditions within healthy adult lungs (37° C., 44 mg/L humidity) can help maintain healthy mucocilliary function in users with respiratory disorders affecting secretion and for all patients humidifying the gas helps maintain comfort and compliance. Several different styles of patient interface assembly 150, such as those disclosed herein, may be used in the example system 100 or a similar system.

Interface Assembly Overview

Figure 2:
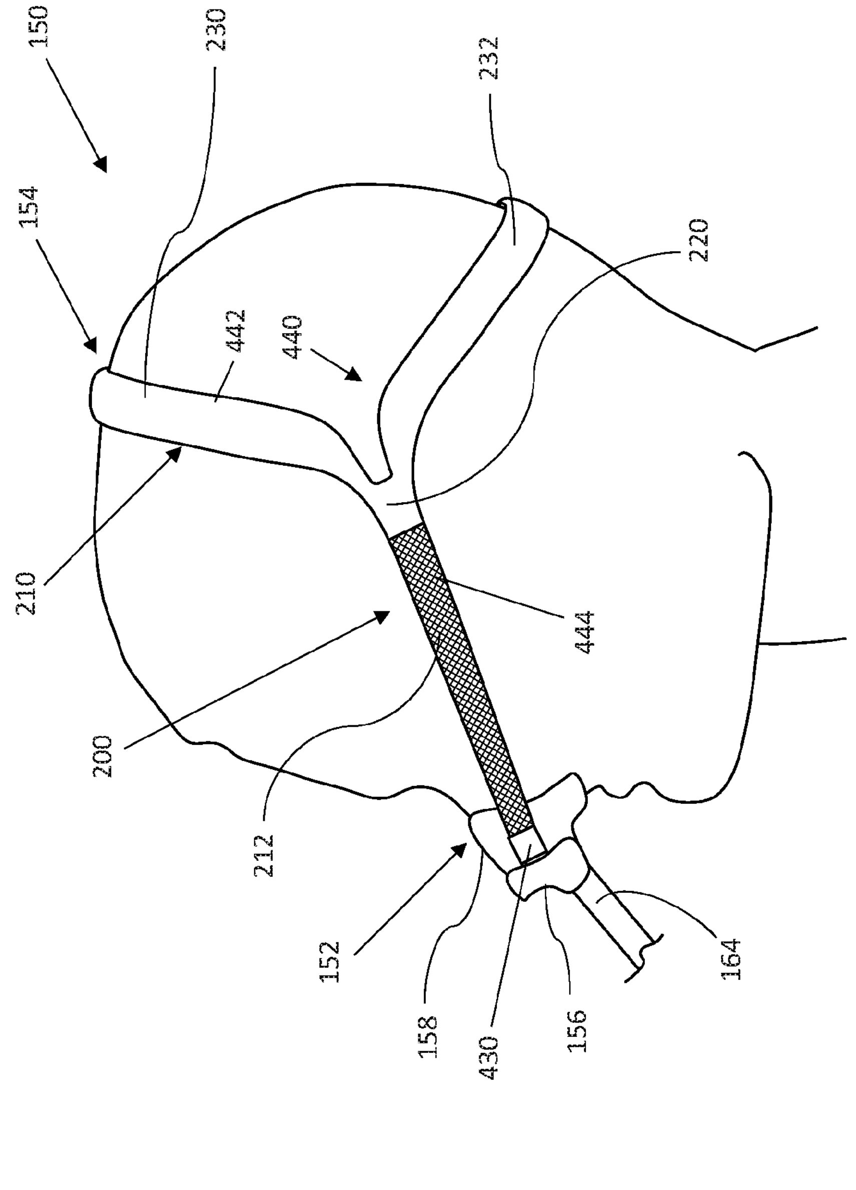
FIG. 2 is a perspective view of a patient interface assembly positioned on a user. The patient interface assembly includes an interface in the form of a nasal mask and a headgear arrangement having a rear portion and a side strap on each side of the rear portion.

FIG. 2 illustrates an example patient interface assembly 150 that can be used in the system 100 of FIG. 1. The patient interface assembly 150 generally includes an interface (e.g., a mask) 152 and a headgear arrangement (“headgear”) 154. The interface 152 is configured to deliver the flow of breathing gases to an airway of the user. The headgear 154 is configured to secure the interface 152 in place on the user.

The illustrated interface 152 is a mask, which can define a breathing chamber. In particular, the illustrated interface 152 is a direct nasal mask having nasal elements (e.g., nasal pillows) configured to deliver the flow of breathing gases directly to the nares of the user. The mask 152 can also create a seal (e.g., a secondary seal) on the user’s face surrounding one or both nares and/or nasal elements. However, other suitable interfaces could also be used with the headgear 154 and/or the headgear 154 could be modified for use with different types of interfaces. For example, the interface could be a nasal mask defining a sealing surface that surrounds one or both of the user’s nares and which omits the direct nasal elements. It will also be appreciated that various features, aspects and advantages of the patient interface assembly 150, while being described in the context of a nasal mask 152, can be used with any other interface configuration, including oronasal masks and full face masks sealing around the user’s nose and mouth, oral masks sealing around the user’s mouth, and nasal pillows or other types of masks sealing under the user’s nose, for example but without limitation.

The mask 152 can include a frame 156 and a cushion or seal 158. The seal 158 can be directly coupled to the frame 156 or can form a portion of a cushion module that is connectable to the frame 156. Such a cushion module can include a relatively rigid housing that is constructed from a material(s) that is harder than the material of the seal 158. The relatively rigid housing can interface with the frame 156. The relatively rigid housing may be removably connected to the frame 156. The relatively rigid housing may incorporate a clip portion that engages with a portion of the frame 156 to connect the cushion module, and thus the seal 158, to the frame 156.

The mask 152 can also include a connection tube 164 configured to connect the mask 152 to a breathing conduit (e.g., the breathing gas circuit 106). The connection tube 164 can be carried by any suitable portion of the mask 152, such as the frame 156 or the cushion module 160 (e.g., the housing). In the illustrated configuration, the connection tube 164 is directly connected to a cooperating portion of the mask 152. The connection tube 164 may be permanently or removably connected to the cooperating portion of the mask 152. In other configurations, the mask 152 can be connected to a breathing conduit by a connector, which can be or include an elbow.

The mask 152 can also include an exhaust or vent to permit expired and excess breathing gases to exit the breathing chamber of the mask 152. In some configurations, the vent can be a bias flow vent comprising a plurality of vent holes. The bias flow vent can be located on the mask frame 156 or on other suitable portions of the mask 152, such as the cushion module or connection tube 164. In some configurations, the bias flow vent can include a diffuser that covers the plurality of vent holes to diffuse the vented gases to reduce the velocity of the vented gases and/or the noise generated by the vented gases. The diffuser can be removable from the mask 152 for cleaning or replacement or can be permanently attached to a portion of the mask 152, such as by an overmolding process that positions a diffuser material into a mold and then injects a suitable plastic material (e.g., polycarbonate) into the mold to create a unitary structure. The diffuser material may be overmolded directly to the frame 156. In other embodiments, the diffuser material may be overmolded to a clip. The clip has engagement portions for engaging complementary engagement features on another part of the mask 152 in order to attach the clip (and the associated diffuser material) to that part of the mask 152.

The headgear 154 is coupled to the mask 152. The headgear 154 can be coupled to the frame 156 of the mask 152. The frame 156 or mask 152 preferably includes a single headgear mount on each side of the frame 156 or mask 152. In the illustrated arrangement, the headgear 154 includes a headgear strap provided on each side of the user's head, which bifurcates at a location generally above the user's ear to form an upper strap portion and a lower strap portion. The straps on each side can be separate from one another or the headgear 154 can form a closed-loop structure that encircles the user's head and has a front connection portion that connects to the frame 156 or mask 152. The headgear 154 is described in further detail below.

Headgear

FIGS. 2-20 illustrate an example of the headgear 154 described above. In the illustrated arrangement, the headgear 154 generally has a front portion 200 and a rear portion 210. The front portion 200 is configured to connect to the mask 152 and extends along each side of the user's head between the mask 152 and the rear portion 210. The rear portion 210 is configured to engage a rearward portion of the user's head.

The illustrated front portion 200 includes a strap 212 on each side of the interface assembly 150 that connects to the mask 152 via a suitable connector, such as a clip. In the illustrated arrangement, the straps 212 on each side of the interface assembly 150 are separate from one another and separately connect to the mask 152. The front straps 212 can be mirror images of one another. Accordingly, details described herein with respect to one strap 212 can be considered to apply to the other strap 212, except in a mirrored fashion, unless otherwise indicated herein.

Each strap 212 extends from the mask 152, across the user's cheek, to a junction 220 with the rear portion 210. Because the straps 212 extend generally along the sides of the user's head, they can be referred to herein as "side straps." In the illustrated arrangement, each side strap 212 extends in a slightly upward direction from an end nearer the mask 152 toward an end nearer the junction 220. Each side strap 212 extends toward or to a location above the user's ear. In some configurations, the rearward end of each of the side straps 212 can be located directly above or above the line of and slightly forward of or slightly rearward of the user's ear.

As described above, the headgear 154 is bifurcated on each side, transitioning from the front portion 200 having the single strap 212 on each side to the rear portion 210 having two strap portions. In particular, the rear portion 210 of the headgear 154 includes a first or upper strap portion or strap 230 and a second or lower strap portion or strap 232. Each of the upper strap 230 and the lower strap 232 are configured to extend around the back of the user's head and connect to the side straps 212. As illustrated in FIG. 2, for example, the upper strap 230 extends in an upward direction from the junction 220 and the lower strap 232 extends in a downward direction from the junction 220. In other words, the upper strap 230 and the lower strap 232 are spaced apart from one another.

In some configurations, the rear portion 210 of the headgear 154 is configured to permit the upper strap 230 and the lower strap 232 to move relative to one another. For example, the rear portion 210 can be configured such that the upper strap 230 and the lower strap 232 can move to allow for adjustment of an angle 240 (FIG. 3) defined between the upper strap 230 and the lower strap 232. The angle 240 can be defined between respective centerlines (e.g., geometric centerlines) of the upper strap 230 and the lower strap 232.

The relative position of the upper strap 230 and the lower strap 232 can also be described by a separation distance 242 (FIG. 5) between the straps 230, 232. The separation distance 242 can be defined as the distance between any two locations on the upper strap 230 and the lower strap 232 in a given relative position of the upper strap 230 and the lower strap 232. For example, the upper strap 230 can have an exterior or upper edge 244 and an interior or lower edge 246. The lower strap 232 can have an interior or upper edge 250 and an exterior or lower edge 252. The separation distance 242 can be defined between an edge 244, 246 of the upper strap 230 and an edge 250, 252 of the lower strap 232. For convenience, the separation distance 242 is illustrated herein as a linear distance between the lower edge 246 of the upper strap 230 and the upper edge 250 of the lower strap 232 taken along a centerline or vertically-oriented, central plane passing through the headgear 154 in a forward-rearward direction.

The rear portion 210 of the headgear 154 can define a particular angle 240 and/or separation distance 242 in a relaxed or neutral position. The relaxed or neutral position may be the position of the rear portion 210 as molded or as defined by the molding tool for a molded embodiment. The relaxed or neutral position may be the position of the rear portion 210 in the absence of an applied external force tending to deform the rear portion 210. Such an angle 240 or separation distance 242 can be referred to as a resting angle 240 or resting separation distance 242.

As described above, the rear portion 210 can be configured to permit relative movement of the upper strap 230 and the lower strap 232 to allow for adjustment of the angle 240 and/or separation distance 242. The rear portion 210 can be configured to permit relative movement of the upper strap 230 and the lower strap 232 resulting in an increase in the angle 240 and/or separation distance 242 relative to an initial angle 240 or separation distance 242, which can be the resting angle 240 or resting separation distance 242. The rear portion 210 can be configured to permit relative movement of the upper strap 230 and the lower strap 232 resulting in a decrease in the angle 240 and/or separation distance 242 relative to an initial angle 240 or separation distance 242, which can be the resting angle 240 or resting separation distance 242. The rear portion 210 can be configured to permit relative movement of the upper strap 230 and the lower strap 232 that results in either an increase or a decrease in the angle 240 and/or separation distance 242 relative to an initial angle 240 or separation distance 242, which can be the resting angle 240 or resting separation distance 242. Such an arrangement allows the rear portion 210 to conform to a wide variety of head shapes and/or user preferences. In addition, the rear portion 210 can be configured to return towards or to the initial angle 240 or separation distance 242, which can be the resting angle 240 or resting separation distance 242, when external forces are removed from the rear portion 210. That is, the rear portion 210 can have an elastic return force as a result of the material selection, shape or combination thereof. In addition, resting separation distance 242 is preferably greater than zero such that some space or gap is provided between the straps 230, 232, which can indicate to user that the straps 230, 232 are designed to provide for separation.

In some configurations, the rear portion 210 is configured such that the upper strap 230 passes over, or can be adjusted to pass over, the top of the user's head from one side to the other side of the headgear 154. The upper strap 230 can be located over the user's parietal bone. In some configurations, the upper strap 230 can be adjustable to be located over the user's frontal bone and/or located over the user's occipital bone. The rear portion 210 can be configured such that the lower strap 232 passes around, or can be adjusted to pass around, the back of the user's head from one side to the other side of the headgear 154. The lower strap 232 can be located over the user's occipital bone. In some configurations, the lower strap 232 can be adjustable to be located over the user's parietal bone.

In some configurations, the rear portion 210 is formed to have a resting angle 240 of between about 60-100 degrees, about 70-90 degrees, or about 75-80 degrees. In some configurations, the rear portion 210 is formed to have a resting angle 240 of about 77 degrees. In some configurations, the rear portion 210 can be adjustable to a minimum angle 240 of less than about 20 degrees, less than about 10 degrees or about 0 degrees—or until the separation distance 242 is zero. In some configurations, the rear portion 210 can be adjustable to a maximum angle 240 of at least about 90 degrees, at least about 120 degrees, at least about 135 degrees, at least about 150 degrees, or at least about 170 degrees. In some configurations, the rear portion 210 can be adjustable to a maximum angle 240 of about 180 degrees or greater.

Figure 7:
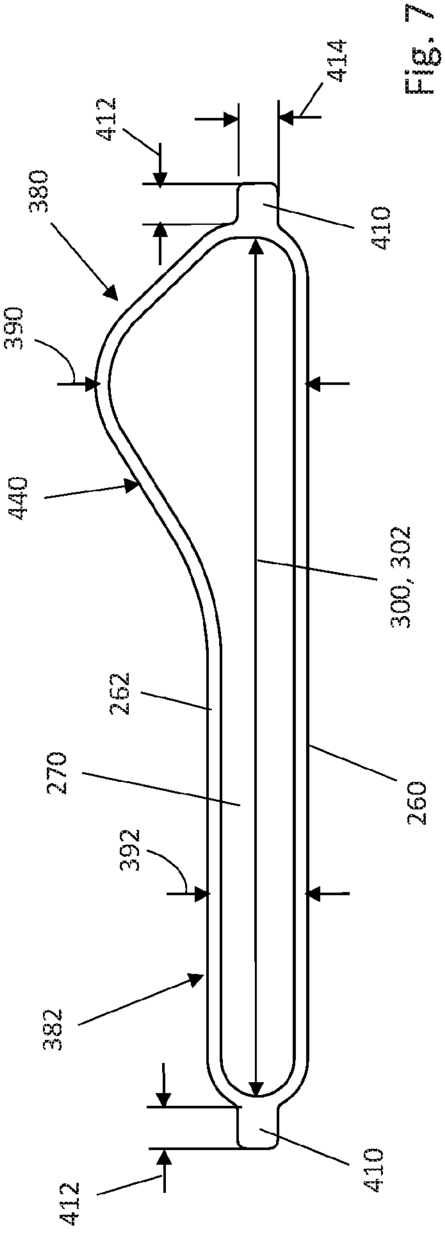
FIG. 7 is a sectional view of the upper strap of the rear portion of FIG. 3, which illustrates a plastic core and a fabric cover, which can be a knitted cover.

At least a portion of the headgear 154 can be constructed as a molded composite structure having at least one fabric layer and at least one plastic layer permanently connected to one another. In some configurations, at least the rear portion 210 is constructed as such a molded composite structure. In the illustrated arrangement, as shown in FIG. 7, the rear portion 210, including the upper strap 230, the lower strap 232 and the junctions 220, is a molded composite structure having two fabric layers (e.g., an interior or inner layer 260 and an exterior or outer layer 262) with a plastic core 270 located between the fabric layers 260, 262. The rear portion 210 can be formed as a unitary structure by the application of molten plastic into the space between the fabric layers 260, 262 within a mold and allowing the molten plastic to harden to form the plastic core 270 in a shape corresponding to the shape of the mold cavity. The fabric layers 260, 262 can be separate from one another and joined via the plastic core 270 or can be connected (e.g., a tubular structure that surrounds the plastic core 270). The composite structure of the rear portion 210 is discussed in further detail below.

A portion or an entirety of the headgear 154 can be semi-rigid. In the illustrated arrangement, any one, any combination or all of the side straps 212, the junctions 220, the upper strap 230 and the lower strap 232 can be semi-rigid. As used herein, semi-rigid means that the semi-rigid portion of the headgear 154 can generally retain its shape under its own weight but has some flexibility to enable the semi-rigid portion to bend around a user's head. In some configurations, the semi-rigid portion of the headgear 154 is more rigid in one direction and is less rigid in a second direction. For example, the semi-rigid portion of the headgear 154 can be substantially rigid in a vertical direction or along the face of the user and can be relatively flexible in a horizontal direction or toward-and-away from the user.

FIGS. 3-6 illustrate the plastic core 270 of the rear portion 210 of the headgear 154 without the fabric layers 260, 262. In the illustrated arrangement, the plastic core 270 of the rear portion 210 is constructed as a unitary body portion comprising a plastic material. That is, the junctions 220, the upper strap 230 and the lower strap 232 are constructed as a one-piece, unitary structure. The upper strap 230 has a first end 280 and a second end 282. A first length or upper strap length 284 is defined between the first end 280 and the second end 282. Similarly, the lower strap 232 has a first end 290 and a second end 292. A second length or lower strap length 294 is defined between the first end 290 and the second end 292. In the illustrated arrangement, the lower strap length 294 is greater than the upper strap length 284. However, in other configurations, the upper strap length 284 can be greater than the lower strap length 294 or the two lengths 284, 294 can be equal or substantially equal.

Figure 5:
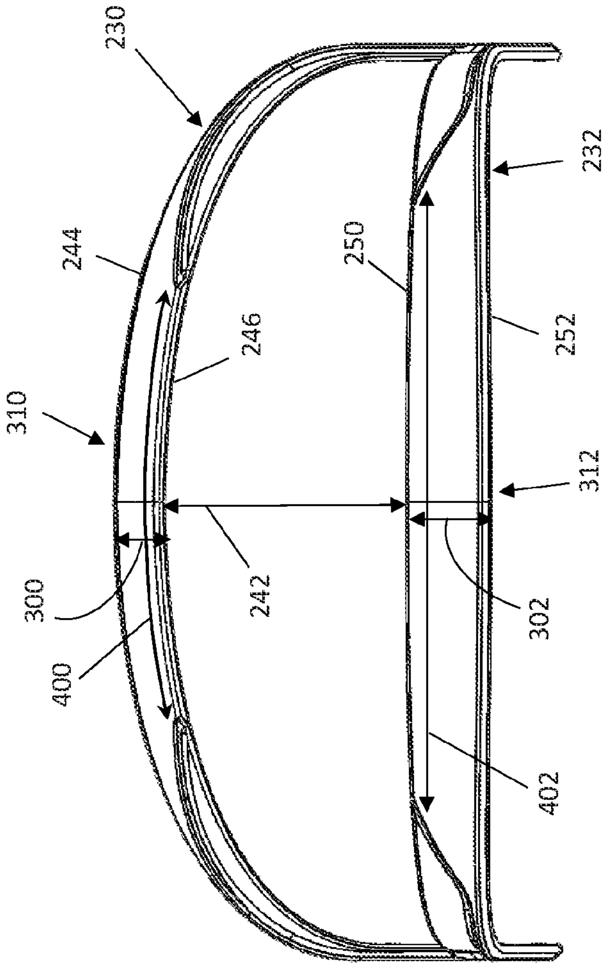
FIG. 5 is a rear view of the rear portion of FIG. 3.

As illustrated in FIG. 5, the upper strap 230 also defines a width 300. Similarly, the lower strap 232 defines a width 302. One or both of the widths 300, 302 can vary along the respective length 284, 294 of the strap 230, 232. For example, the width 300, 302 at or near the ends 280, 282, 290, 292 of the straps 230, 232 can be smaller than the width 300, 302 at or near a respective central portion 310, 312 of the upper strap 230 and the lower strap 232. In the illustrated arrangement, the width 302 of the lower strap 232 is greater than the width 300 of the upper strap 230. The width 302 of the lower strap 232 can be greater than the width 300 of the upper strap 230 at corresponding positions (e.g., ends 280, 282, 290, 292 or central portions 310, 312). Alternatively or in addition, the width 302 along an entirety of the lower strap 232 can be greater than the width 300 along an entirety of the upper strap 230. In other words, a minimum value of the width 302 of the lower strap 232 can be greater than a maximum value of the width 300 of the upper strap 230. The difference in width 300, 302 between the upper strap 230 and the lower strap 232 can assist the user in differentiating between the straps 230, 232 and, therefore, properly orienting the rear portion 210 and/or the headgear 154. In some configurations, the width 300 of the upper strap 230 is about 15 mm and the width 302 of the lower strap 232 is about 17.5 mm. These widths 300, 302 can be the minimum widths, maximum widths or the average widths of the straps 230, 232.

As described above, the rear portion 210 of the headgear 154 is configured to permit relative movement between the upper strap 230 and the lower strap 232 to allow for adjustment of the angle 240 or separation distance 242 between the straps 230, 232. In some configurations, a substantial portion or an entirety of the relative movement is provided by the junctions 220 between the ends 280, 282, 290, 292 of the straps 230, 232. Each of the junctions 220 can be configured to allow for or facilitate relative movement between the straps 230, 232. The junctions 220 can allow for or facilitate movement of one or both of the upper strap 230 and the lower strap 232 relative to the junction 220. In the illustrated arrangement, the junctions 220 are mirror images of one another. Accordingly, one junction 220 is described herein for convenience. The description of the one junction 220 can equally apply to the other junction 220, except in a mirrored fashion, unless otherwise indicated.

Figure 4:
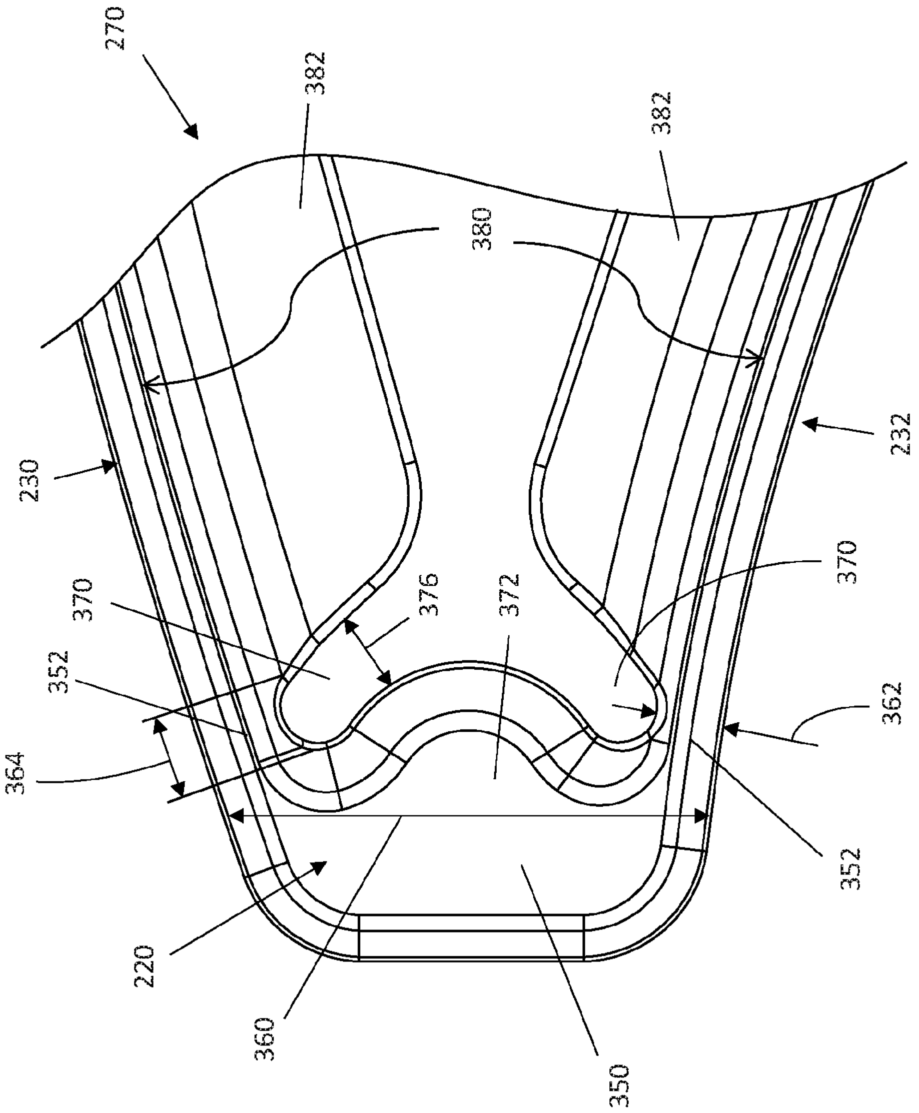
FIG. 4 is an enlarged perspective view showing a junction between an upper strap and a lower strap of the rear portion of FIG. 3, which is configured for adjustment of a separation between the upper strap and the lower strap.

With reference to FIG. 4, the junction 220 comprises a base portion 350, which may be an end portion (e.g., a forward end portion) of the junction 220. The junction 220 also includes a transition region 352 between the base portion 350 and one or both of the upper strap 230 and the lower strap 232. In the illustrated arrangement, each of the upper strap 230 and the lower strap 232 are joined to the base portion 350 of the junction 220 by a transition region 352 (e.g., a first transition region and a second transition region). The transition regions 352 are discrete from one another and are separated by the base portion 350. However, in other arrangements, the transition regions 352 could be connected with one another or a single transition region 352 could join both the upper strap 230 and the lower strap 232 to the base portion 350.

Each of the transition regions 352 is configured to allow for movement (e.g., angular movement) of the respective strap 230, 232 relative to the base portion 350 of the junction 220. In some configurations, the transition regions 352 also permit torsional movement of the respective strap 230, 232, which can allow the straps 230, 232 to better conform to the head shape of the particular user. The transition regions 352 can allow for or facilitate this movement by any suitable mechanism, such as size and/or shape of the transition region 352, material selection, or a combination thereof. In the illustrated arrangement, the transition regions 352 are local regions of reduced size (e.g., width and/or thickness) relative to one or both of the base portion 350 and the associated strap 230, 232.

The structure of the junction 220 and straps 230, 232 adjacent and including the transition regions 352 form a flex region 354, which allows for or facilitates the above-described movement. The flex regions 354 include the transition regions 352 and may include portions of the base portion 350 of the junction 220 and portions of the straps 230, 232. That is, flexural movement of the upper strap 230 and/or the lower strap 232 relative to the base portion 350 may result in some flex or deformation of portions of the base portion 350 and/or portions of the straps 230, 232 adjacent the transition regions 352. The flex regions 354 are generally indicated by the dashed line areas shown in FIG. 3. The flex regions 354 can be substantially similar in size as the transition regions 352 relative to substantially larger structures of the rear portion 210, such as the base portion 350 of the junctions 220 and the straps 230, 232. Accordingly, the dimensions and relative sizes described herein with respect to the transition regions 352 can equally apply to the flex regions 354.

The transition regions 352 and/or the structure of the junction 220 and straps 230, 232 adjacent and including the transition regions 352 and/or the flex regions 354 can form a living hinge arrangement. A living hinge, which can sometimes be called a flexure joint, flexure bearing or flex bearing, is a flexible segment or portion of material that joins two relatively more rigid segments or portions. The hinge is flexible, allowing it to bend, and allowing movement of the attached segments or portions. A living hinge is typically made from the same material as the two more rigid portions it connects, which is the case with the unitary rear portion 210 disclosed herein. The living hinge is typically thinned or cut to allow the rigid portions to bend along the line of the hinge. A living hinge does not include a defined pivot structure. The low wear and minimal friction in a living hinge makes it advantageous for the adjustable rear portion 210, which may be exposed to many adjustment cycles and may be used by persons having low hand strength and/or dexterity. The living hinges can be substantially similar in size as the transition regions 352 and/or the flex regions 354 relative to substantially larger structures of the rear portion 210, such as the base portion 350 of the junctions 220 and the straps 230, 232. Accordingly, the dimensions and relative sizes described herein with respect to the transition regions 352 and/or the flex regions 354 can equally apply to the living hinges.

The base portion 350 defines a width 360, which may be a maximum width. Each transition region 352 also defines a width 362, which may be a minimum width. The width 362 of the transition region 352 can be less than the width 360 of the base portion 350. The width 362 of the transition region 352 can be less than the width 300, 302 of the associated strap 230, 232 to which the transition region 352 is joined. The width 362 of the transition region 352 can be less than both the width 360 of the base portion 350 and the width 300, 302 of the associated strap 230, 232.

The reduced width 362 of the transition regions 352 can facilitate rotational movement of the straps 230, 232 to allow for adjustment of the relative positions of the straps 230, 232, as described above. In some configurations, the width 362 of the transition region 352 is less than about one-half or less than about one-third of the width 300, 302 of the respective one of the upper strap 230 or the lower strap 232 to which the transition region 352 is joined. In some configurations, the width 362 of the transition region 352 is less than about 10 mm, less than about 8 mm, or less than about 7 mm. In some configurations, the width 362 of the transition region 352 is about 3 mm-7 mm, or about 5 mm.

The transition region 352 defines a length 364, which can be the length of the reduced width portion of the junction 220 between the base portion 350 and the associated strap 230, 232. As described above, preferably the transition region 352 is a localized region of reduced size. Accordingly, a size (e.g., the length 364) of the transition region 352 is small in comparison to a size (e.g., the length 284, 294) of the associated strap 230, 232. In some configurations, the length 364 of the transition region 352 is less than the width 360 of the base portion 350 and/or the width 300, 302 of the respective one of the upper strap 230 or the lower strap 232 to which the transition region 352 is joined. In some configurations, the length 364 of the transition region 352 is less than about two-thirds or one-half of the width 300, 302 of the respective one of the upper strap 230 or the lower strap 232 to which the transition region 352 is joined. In some configurations, the length 364 of the transition region 352 is less than about 10 mm, less than about 8 mm, or less than about 7 mm. In some configurations, the length 364 of the transition region 352 is about 3 mm-7 mm, or about 5 mm.

Each of the transition regions 352 is at least partially defined by a slot 370, which is formed by the plastic core 270 of the rear portion 210. In the illustrated arrangement, the slots 370 are connected to one another. The slots 370 are also connected to the space between the upper strap 230 and the lower strap 232 (between the lower edge 246 and the upper edge 250). In the illustrated arrangement, the slots 370 cooperate to define a generally arcuate or part-annular-shaped opening. The slots 370 are also partially defined by a rounded protrusion 372 of the base portion 350. In some configurations, the slots 370 are sized and/or shaped similarly to one another. In some configurations, the junction 220 can be symmetrical or substantially symmetrical about an axis 374 (FIG. 3) that passes through the junction 220 and between the upper strap 230 and the lower strap 232. Each slot 370 can define a width 376 (e.g., a maximum width). The width 376 of the slot 370 can be less than the width 360 of the base portion 350 and/or the width 300, 302 of the respective one of the upper strap 230 or the lower strap 232 located adjacent the slot 370.

In the illustrated arrangement, each of the upper strap 230 and the lower strap 232 include a relatively stiffer or reinforced portion, which is referred to herein as a main strap portion 380. Preferably, one or both of the upper strap 230 and the lower strap 232 also include one or more relatively less stiff portions, which are referred to herein as flange portions 382. The main strap portion 380 is in the form of a thickened rib in comparison to the flange portions 382. The main strap portions 380 can be configured to accommodate a substantial portion or an entirety of the tensile forces applied to the rear portion 210 of the headgear 154 as a result of normal use, such as blow-off forces and/or hose-pull forces, for example. The flange portions 382 can be configured to spread the forces applied to the user's head over a larger area relative to the main strap portions 380 alone. The flange portions 382 can also be more flexible than the main strap portions 380 to provide the rear portion 210 of the headgear 154 with variable flex characteristics along a width and/or a length of the straps 230, 232.

With reference to FIG. 7, the main strap portions 380 can define a first thickness 390 and the flange portion 382 can define a second thickness 392. The second thickness 392 can be smaller than the first thickness 390. Or, stated another way, the first thickness 390 can be larger than the second thickness 392. In some configurations, the first thickness 390 can be between about 1.5-5 mm, between about 2-3 mm, or between about 2-2.5 mm. The second thickness 392 can be between about 1-2.5 mm, between about 1-2 mm, or between about 1-1.5 mm. The relative thicknesses 390, 392 can include any value or relative proportion covered by the above ranges or dimensions. The thicknesses 390, 392 can include or omit the cover layer(s) 260, 262. Dimensions of the cover layers 260, 262 are described further below.

In the illustrated configuration, the main strap portion 380 of extends along an entirety or a substantial entirety of the length 284, 294 of one or both of the upper strap 230 and the lower strap 232. With such an arrangement, the rear portion 210 of the headgear 154 has sufficient strength or stiffness to accommodate the expected forces in use. As shown in FIG. 4, for example, the base portion 350 of the junction 220 can have a thickness that is the same as or similar to the thickness 390 of the main strap portion 380. The main strap portion 380 and/or the base portion 350 can be rounded or taper toward the edges, as shown in FIGS. 4 and 7, to avoid edges that may reduce comfort or provide the appearance of reduced comfort to a user. As shown the base portion 350 can also be rounded or tapered towards the slots 370.

In some configurations, the main strap portion 380 is provided along an edge of one or both of the straps 230, 232. In some configurations, the main strap portion 380 defines an entirety of an edge of one or both of the strap 230, 232. In the illustrated arrangement, the main strap portion 380 defines an entirety of the upper edge 244 of the upper strap 230. However, the main strap portion 380 could define less than an entirety of the upper edge 244. In the illustrated arrangement, the main strap portion 380 defines an entirety of the lower edge 252 of the lower strap 232. However, the main strap portion 380 could define less than an entirety of the lower edge 252. Such an arrangement promotes torsion within the straps 230, 232 resulting in the upper edge of the upper strap and the lower edge of the lower strap being positioned forward or anterior of the respective lower edge of the upper strap and the upper edge of the lower strap. Such an orientation of the straps 230 232 suits or accommodates most head shapes. In other configurations, these arrangements could be reversed and the main strap portions 380 could define a portion or an entirety of the lower edge 246 of the upper strap 230 and/or the upper edge 250 of the lower strap 232.

Preferably, the flange portions 382 extend along a substantial portion of the lengths 284, 294 of the straps 230, 232. In some configurations, the flange portions 382 extend along only a portion of the lengths 284, 294. In the illustrated arrangement, a flange portion 382 is provided on each side of the central portion 310, 312 of each of the upper and lower straps 230, 232. Together, the flange portions 382 of each strap extend along at least about one-half, at least about two-thirds, or about two-thirds of the length 284, 294 of the strap 230, 232. The flange portions 382 can be configured to extend along a substantial entirety of a respective side of the user's head in use.

As illustrated in FIG. 5, the central portions 310, 312 of each illustrated strap 230, 232 are defined entirely by the main strap portions 380. In other words, the main strap portions 380 extend the entire width 300, 302 of the straps 230, 232 within a portion or entirety of the central portions 310, 312. In the illustrated arrangement, the main strap portions 380 taper in width on each side of the central portions 310, 312 and the flange portions 382 correspondingly taper in width in a direction from the side or ends of the rear portion 210 toward the central portions 310, 312.

In some configurations, the main strap portion 380 or the main strap portion 380 and the flange 382 together define an entirety of the width 300, 302 of the strap 230, 232 at any location along the length 284, 294 of the strap 230, 232. As noted above, in the illustrated arrangement, the main strap portion 380 defines an entirety of the width 300, 302 of the central portion 310, 312 of the strap 230, 232. Such an arrangement can allow the straps 230, 232 to maintain a relatively large arc in a neutral state to facilitate donning and doffing by the user. In addition, the loading on the central portions 310, 312 (rear portions when worn) is greater than the loading on the end portions (side portions when worn). Accordingly, greater resistance to twisting and/or folding is desirable for the central portions 310, 312.

In some configurations, a length 400 of the central portion 310 or the main strap portion 380 within the central portion 310 of the upper strap 230 can be different than a length 402 of the central portion 310 or the main strap portion 380 within the central portion 310 of the lower strap 232. As illustrated in FIG. 5, the length 400 of the upper strap 230 is less than the length 402 of the lower strap 232. Thus, the lower strap 232 can have a larger arc (e.g., larger diameter) than the upper strap 230, which can facilitate differentiation of the straps 203, 232 by the user and/or better fit a typical user's head shape. In some configurations, the length 400 can be between about 50 mm-100 mm, between about 60 mm-90 mm, between about 70 mm-80 mm, or about 75 mm.

The length 402 can be between about 75 mm-125 mm, between about 85 mm-115 mm, between about 95 mm-105 mm, or about 100 mm. In other configurations, this arrangement could be reversed and the length 400 can be greater than the length 402 or the lengths 400, 402 could be the same. The lengths 400, 402 can be defined as the maximum length, the minimum length or the average length of the main strap portion 380 within the central portion 310, 312.

Figure 3:
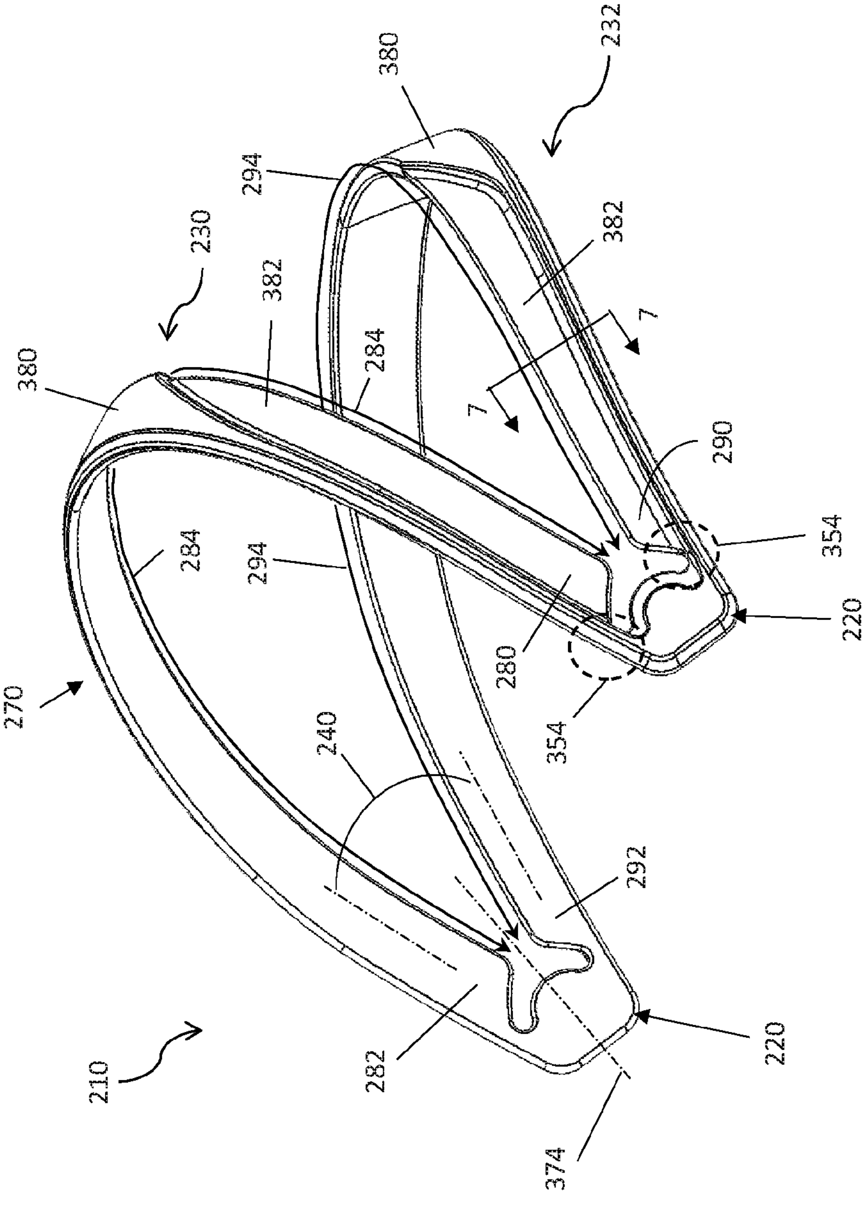
FIG. 3 is a perspective view of the rear portion of the headgear arrangement of FIG. 2.
Figure 6:
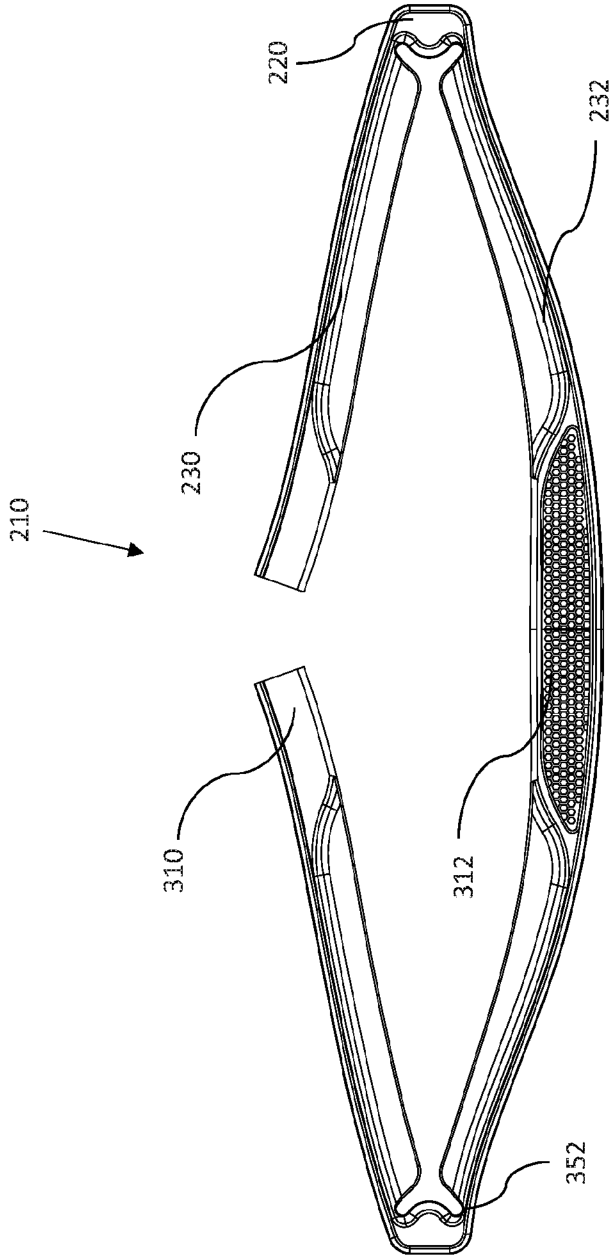
FIG. 6 is a rear view of an alternative arrangement of the rear portion of FIG. 3 shown in a laid-flat configuration.

As noted above, the rear portion 210 can be constructed from or comprise a molded plastic structure. In the illustrated arrangement, the rear portion 210 includes a unitary plastic structure (e.g., the plastic core 270). The plastic core 270 can be molded in a three-dimensional shape, as shown in FIGS. 3-5, for example. The three-dimensional molded shape can be the same as or similar to a neutral shape of the rear portion 210. In other configurations, the plastic core 270 can be molded in a different shape, such as a flat shape. The flat plastic core 270 can be formed into shape by the user, such as when the headgear 154 is applied to the user's head. In other configurations, the flat plastic core 270 can be formed into a three-dimensional shape during the manufacturing process or otherwise prior to use. For example, as illustrated in FIG. 6, one or both of the upper strap 230 or the lower strap 232 (the upper strap 230 in the illustrated example) can be split or divided into two pieces as molded or otherwise formed. The ends of the divided strap 230, 232 can then be joined by a suitable coupling arrangement or process, such as by an adhesive joint, for example. As also described above, the rear portion 210 can also include one or more fabric layers 260, 262. The ends of the divided strap 230, 232 can also be joined, in whole or in part, by the fabric layer(s) 260, 262.

The plastic core 270 can be constructed from any suitable material or combination of materials. In some configurations, the plastic core 270 can be constructed from a thermoplastic elastomer (TPE) material, such as a polyether block amide (PEBA). An example of such a material is sold under the Pebax® brand name by Arkema S. A. of Colombes, France. In particular, the material can be Pebax® 2533. In some configurations, the material can have a shore hardness of between about 10-40 Shore D, about 20-30 Shore D, or about 22-27 Shore D. Such materials can result in the plastic core 270 having some elasticity or that allows some amount of stretch. The fabric layers 260, 262 or other covering can modify the elasticity of the plastic core 270, as discussed further below. The plastic core 270 could alternatively be constructed from a silicone material, which can provide a desirable amount of flexibility. Lower shore hardnesses, such as within the ranges identified above, creates a "firm textile" feel to the rear portion 210 of the headgear 154. In other words, the rear portion 210 of the headgear 154 is perceived by users as a firm fabric strap, instead of a plastic strap with a fabric covering. Advantageously, the disclosed rear portions 210 provides the characteristics of classic fabric headgear straps, such as the soft texture, tactile feel, visual appeal and flexibility, but with the shape memory of plastic. The upper and lower straps 230, 232 are flexible, but the structure of the rear portion 210 of the headgear 154 is maintained without the straps 230, 232 collapsing or tangling like classic fabric straps. Such an arrangement increases usability and convenience of the headgear 154.

Figure 8:
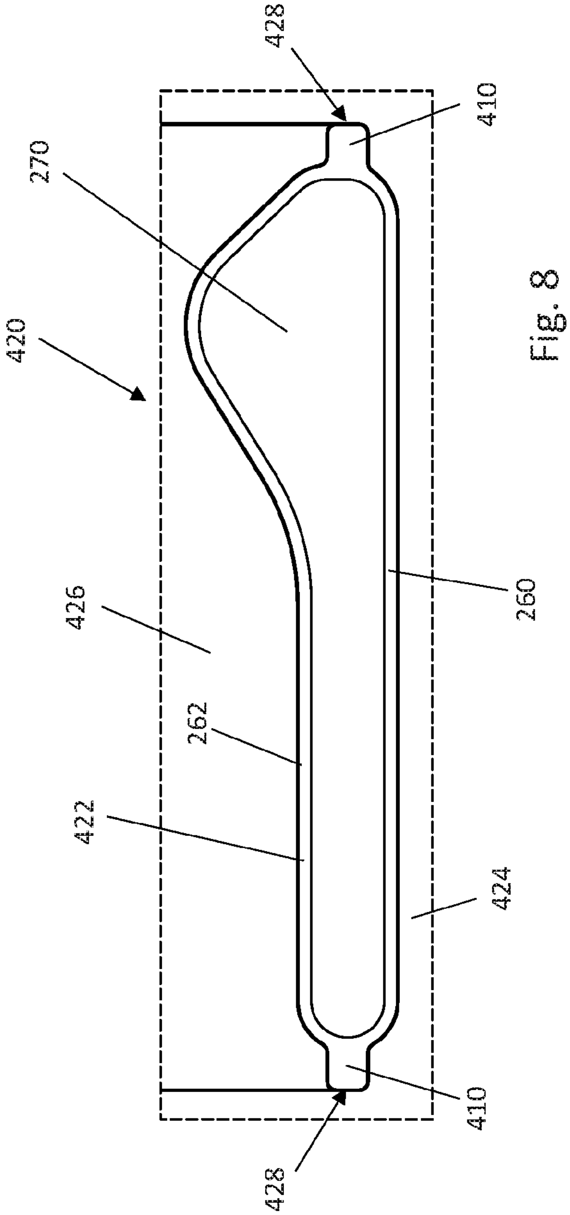
FIG. 8 is a sectional view of the upper strap within a molding tool.

With reference to FIGS. 7 and 8, as described above, the plastic core 270 can be covered by one or more fabric layers, such as the layers 260, 262. In some configurations, only one side (e.g., an interior or an exterior side) of the plastic core 270 is covered by a fabric layer. In the illustrated arrangement, both of the interior side and the exterior side of the plastic core 270 are covered by the fabric layers 260, 262. As described above, the fabric layers 260, 262 can be separate from one another (and joined by the plastic core) or can be joined directly to one another. As described above and further herein below, the fabric layers 260, 262 can be formed as a single structure (e.g., a tubular structure, such as a tubular knitted structure).

As formed, the fabric layers 260, 262 can be positioned adjacent one another or joined along the edges (e.g., upper and lower edges in use) of the plastic core 270 between the interior side and the exterior side. The fabric layers 260, 262 can be configured to have protruding edge 410 on each of the upper and lower edges. The protruding edges 410 can be defined by a length of the fabric layer(s) 260, 262 that extend beyond the plastic core 270. The protruding edges 410 can provide increased padding along the edges of the plastic core 270 relative to a design without protruding edges 410 and, thus, greater comfort and/or the appearance of greater comfort for the user. In some configurations, the protruding edges 410 can have a width 412 of between about 0.5 mm-3 mm, between about 0.75 mm-2 mm, or about 1 mm. In some configurations, the protruding edges 410 can have a thickness 414 of between about 0.3 mm-2 mm, between about 0.4 mm-1 mm, about 0.4 mm, or about 0.3 mm. A thickness of each layer 260, 262 can be between about 0.2 mm-1 mm, between about 0.2 mm-0.5 mm, or about 0.2 mm. Thus, in some configurations, a width and/or a thickness of the protruding edges 410 can be greater than a thickness of the individual layers 260, 262. The protruding edges 410 could also include an air (or other gas) space between the layers 260, 262 to provide additional comfort. In some configurations, the protruding edges 410 are provided along the upper strap 230 and the lower strap 232 of the rear portion 210. The protruding edges 410 also can be provided on an outer edge of the junctions 220. However, preferably, the protruding edges 410 are omitted from the interior edge of the junctions 220 defined by the slot(s) 370. Such an arrangement can increase the flexibility or at least avoid inhibiting the flexibility of the upper strap 230 and/or the lower strap 232 as a result of the additional bulk that would otherwise be present if the protruding edges 410 were provided along the interior edge of the junctions 220.

FIG. 8 illustrates a mold tool 420 that can be used to form the rear portion 210 of the headgear 154. As described above, the fabric layers 260, 262 can be positioned within a cavity 422 the portions or halves 424, 426 of the mold tool 420. The mold tool 420 includes shut-off portions 428 that form the protruding edges 410 of the fabric layer(s) 260, 262. The shut-off portions 428 can define a space sized and shaped to accommodate the protruding edges 410, but that are small enough that little or no plastic material is able to enter. Accordingly, the plastic core 270 can have the shape as illustrated in the figures with rounded upper and lower edges as defined by the shape of the portions of the mold tool 420 adjacent the shut-off portions 428. To form the plastic core 270 and permanently couple the fabric layer(s) 260, 262 to the plastic core 270, molten plastic material is introduced into the cavity 422 of the mold tool 420 between the fabric layers 260, 262 and allowed to harden.

As shown in FIG. 2, the fabric layers 260, 262 can also extend along a portion or an entirety of the front portion 200 or the side straps 212 of the headgear 154. It can be desirable for the side straps 212 to be capable of varying in length to allow the headgear 154 to fit different users and/or to facilitate donning and doffing of the headgear 154. In some configurations, the headgear 154 is configured to provide for simple adjustment to a suitable size for an individual user.

In some configurations, the mask assembly 150 may employ one or more directional locks 430 (FIGS. 2 and 12) that provide for different resistance to different directions of movement between the mask 152 and the headgear 154. For example, the directional lock(s) 430 can provide a first resistance to movement of the mask 152 and the headgear 154 in a first direction away from one another thereby increasing the circumference or perimeter of the closed loop defined by the mask 152 and headgear 154. The directional lock(s) 430 can provide a second resistance to movement of the mask 152 and the headgear 154 in a second direction towards one another thereby reducing the circumference or perimeter of the closed loop defined by the mask 152 and headgear 154. The first resistance force is greater than the second resistance force.

With such an arrangement, there is relatively low resistance to reducing the perimeter of the closed loop for easy fitment to the user and relatively higher resistance to increasing the perimeter of the closed loop to inhibit or prevent increasing the perimeter of the closed loop in response to normal or expected forces during use, such as blow-off and/or hose pull forces, for example. Preferably, the first resistance force is configured such that it can be overcome by manual force applied by the user to allow for donning or doffing of the mask assembly 150. In addition, the second resistance force is low enough that a relatively small elastic force can be provided by a suitable elastic member (or spring or biasing arrangement) to automatically move the mask 152 and headgear 154 towards one another to reduce the closed loop perimeter towards or to a suitable size for a particular user.

In use, the user can place the mask 152 in position on his or her face and pull on the rear portion 210 of the headgear 154, overcoming the first resistance force provided by the directional lock(s) 430, to increase the closed loop perimeter length so the rear portion 210 of the headgear 154 can be positioned onto the rear portion of the user's head. The user can release the rear portion 210 of the headgear 154 and a suitable elastic member can reduce the closed loop perimeter, overcoming the second resistance force provided by the directional lock(s) 430, to move the mask assembly 150 towards or to a suitable closed loop perimeter length for the particular user. Once therapy begins, the directional lock(s) 430 inhibit or prevent an increase in the closed loop perimeter length in response to normal or expected forces during use. Once therapy ends, the user can grasp the rear portion 210 of the headgear 154 and increase the closed loop perimeter length, overcoming the first resistance force, to remove the mask assembly 150.

In some configurations, as described above, the side straps 212 provide for the variation in the closed loop perimeter length of the mask assembly 150. In addition, the side straps 212—in particular, the fabric layer(s) 260, 262—provide the elastic force tending to reduce the closed loop perimeter length against the second resistance force offered by the directional lock(s) 430. In some configurations, a directional lock 430 is located on each side of the mask assembly 150. The directional locks 430 can be carried by the mask 152 and can interact with a portion of the associated side strap 212. Thus, the first resistance force can resist lengthening movement of the associated side strap 212 and the second resistance force can resist shortening movement of the associated side strap 212. The side straps 212 can extend between and be connected to the mask 152 and the rear portion 210 of the headgear 154 and apply an elastic or biasing force tending to shorten the side straps, reduce the closed loop perimeter length or move the mask 154 towards the rear portion 210 of the headgear.

In some configurations, the fabric layers 260, 262 cooperate to form a cover 440 for both the front portion 200 and the rear portion 210 of the headgear 154. The cover 440 can be a unitary structure. In some configurations, the portion 442 of the cover 440 located on the rear portion 210 of the headgear 154 is inelastic or relatively inelastic and the portion 444 of the cover 440 located on the front portion 200 or side straps 212 of the headgear 154 is elastic or relatively elastic. As described above, the cover 440 can be formed by a knitted structure. An advantage to a knitted structure is that the relatively inelastic portion 442 and the relatively elastic portion 444 can be formed as a unitary or single piece construction.

As described above, the plastic core 270 can be constructed from a material having some elasticity or that allows some amount of stretch. The inelastic material, relatively inelastic material or the general inelastic characteristic of the rear portion 442 of the cover 440 can modify the elasticity or the ability to stretch of the plastic core 270. As a result of the combination of the elastic or stretchable material of the core 270 with the inelastic material of the cover 440, the rear portion 210 can be relatively inelastic or substantially inelastic, but can provide an advantageous level of flexibility. The permanent connection between the cover 440 and the plastic core 270 can facilitate or enhance the relatively high level of flexibility with little or no more than an acceptable amount of stretch. The resulting rear portion 210 can be considered non-stretch or substantially non-stretch. As used herein, a substantially non-stretch headgear component exhibits no more than an acceptable amount of stretch, which is capable of maintaining the interface in place on the face of the user in a suitable position to deliver the desired therapy.

In some configurations, the tubular knitted cover 440 can be formed by a suitable knitting process using suitable materials, such as the processes and materials described herein. The knitted cover 440 can be formed as a single piece including one or more of the side straps 212, the upper strap 230 and the lower strap 232. In other words, the knitted cover 440 can be formed by knitting a single piece that includes a bifurcation from the side strap 212 into the upper and lower strap 230, 232 via the junctions 220.

The knitted cover 440 can be knitted into a shape that approximates or substantially matches the final shape of the headgear 154 as partially determined by the cavity of the mold tool 420. With such an arrangement, the stitch structure and knit direction generally or substantially matches the shape of the plastic core 270 as determined by the cavity of the mold tool 420. The resulting rear portion 210 of the headgear 154 possesses knitted edges that match the curvature of the plastic core 270 and can reduce material build-up and/or bunching in comparison to fabric coverings made from flat sheet material.

With reference to FIGS. 1 and 9A-10, as noted above, different portions 442, 444 of the cover 440 can be constructed with different materials or different combinations of materials. For example, in the illustrated arrangement, rear or inelastic portion 442 of the knitted cover 440 is created using a first material 450 (e.g., the hatched thread in FIG. 10), such as a first yarn or filament type. In some configurations, the first material 450 is or comprises nylon (e.g., textured nylon). Textured nylon provided bulk and stability at the back of the user's head and a texture that is comfortable for the user. In the illustrated arrangement, the front portion 200 or side straps 212 uses a second material 452

(e.g., the non-hatched thread in FIG. 10), such as a second yarn or filament type. In some configurations, the second material 452 is or comprises an elastane material (e.g., Lycra). In some configurations, the second material 452 is a nylon-wrapped (e.g., double nylon-wrapped) elastane.

Figure 10:
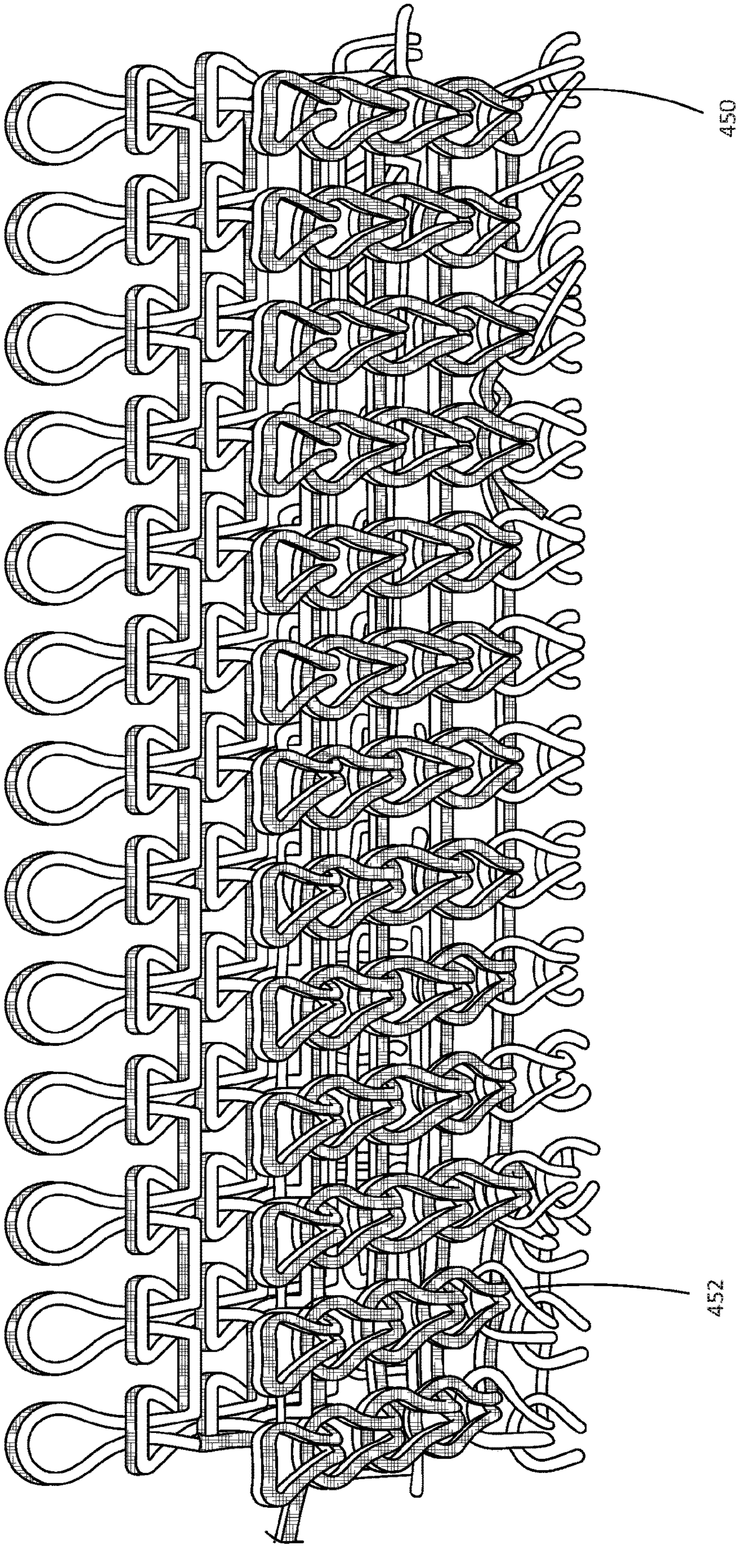
FIG. 10 illustrates a transition between an inelastic portion and an elastic portion of the knitted fabric covering.

A transition between the rear portion 442 and the front portion 444 can include both the first and second materials 450, 452, as illustrated in FIG. 10. In the transition, both the first and second materials 450, 452 are knitted for a certain number of wales. Such a process is referred to as plating. The purpose of the transition and the plating is to provide reinforcement and strength to the junction between the inelastic portion 442 and the elastic portion 444. In some configurations, the plating could be extended to a substantial portion or an entirety of one of the upper strap 230 or the lower strap 232. Such an arrangement could provide a different texture between the straps 230, 232 and assist the user in differentiating between the upper strap 230 and the lower strap 232.

In some configurations, the cover 440 can be knitted from side-to-side beginning with one side strap 212, progressing to the upper and lower straps 230, 232 of the rear portion 210 and finishing with the other side strap 212. Alternatively, cover 440 could be knitted from top-to-bottom or bottom-to-top. At the transition between the first side strap 212 and the rear portion 201, the plating procedure described above can be applied to one of the upper strap 230 or the lower strap 232 to transition from the second material 452 to the first material 450. When yarn or filament of the second material 452 of the elastic portion 444 is cut in the one of the upper strap 230 or the lower strap 232, an additional yarn or filament of the first material 450 can be introduced and can be knitted to form the other of the upper strap 230 and the lower strap 232. Once the rear portion 210 is knitted, the plating procedure can be repeated and the second side strap 212 can be formed from the second material 452.

Figure 9B:
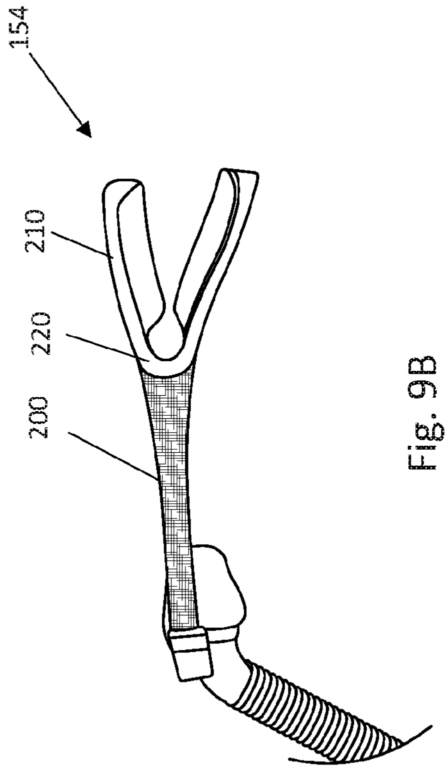
FIGS. 9A-9D illustrate a portion of several alternative arrangements of the headgear arrangement showing several junction shapes and patterns of the knitted fabric cover.
Figure 9C:
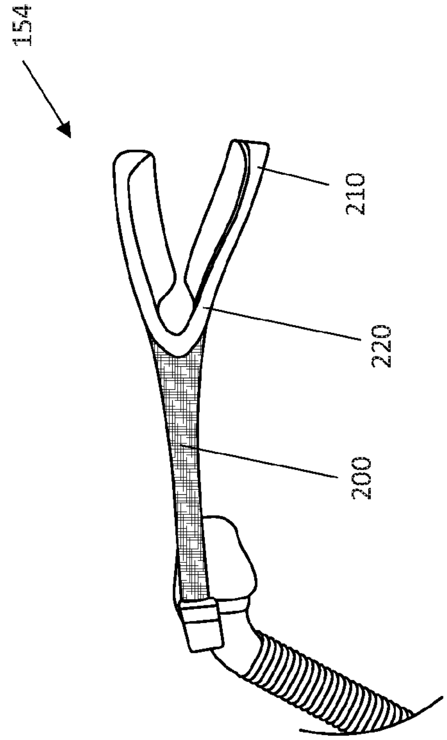
Figure 9A:
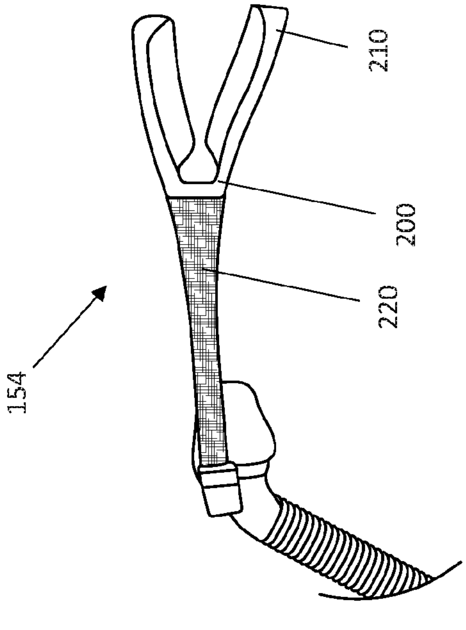
Figure 9D:
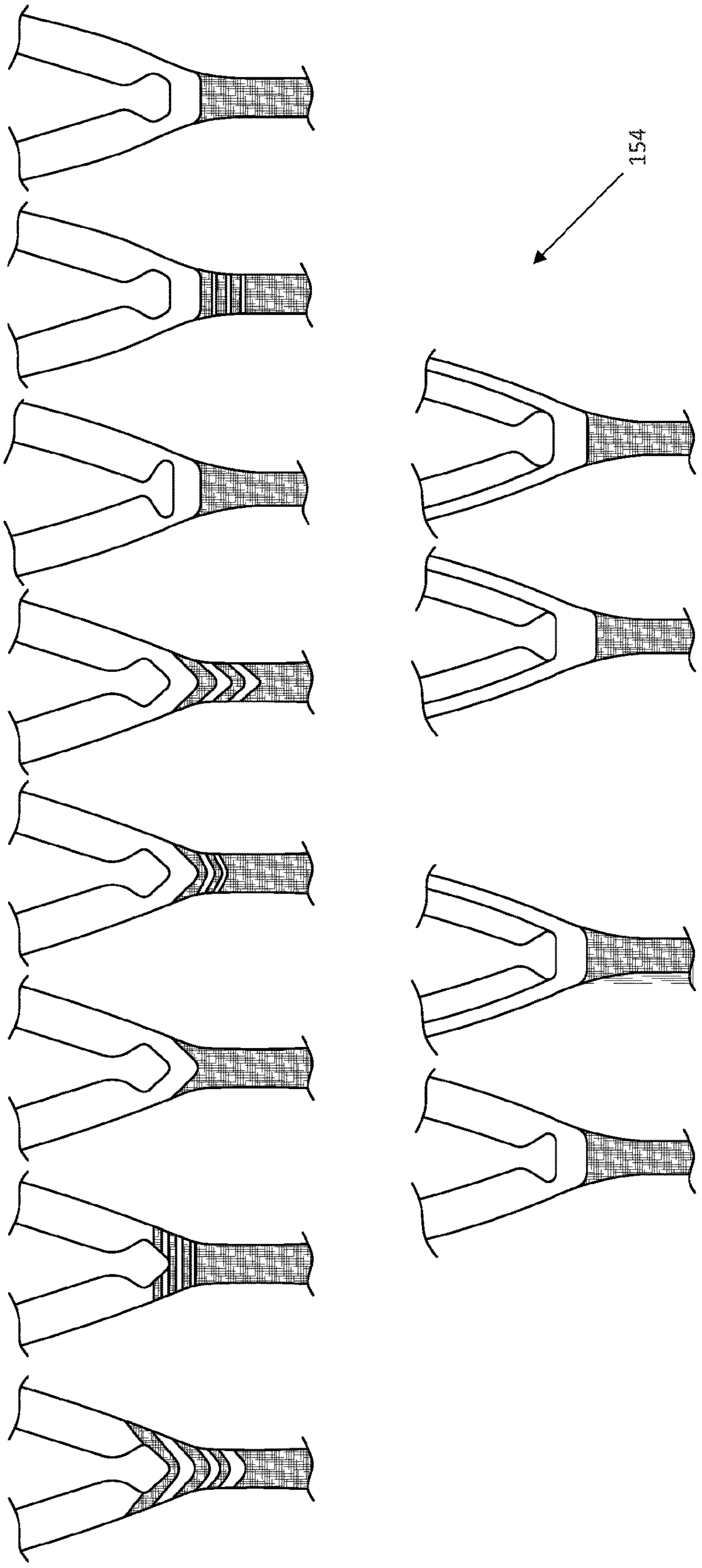

With reference to FIGS. 2 and 9A-9D, the materials used to construct the cover 440 can vary to provide the headgear 154 with variation in color, pattern and/or texture to facilitate differentiation between different portions of the headgear 154 (e.g., between the straps 212, 230, 232) or to provide visual or textural interest, or both. As illustrated in FIGS. 2 and 9A-9D, a portion or an entirety of the rear portion 210 of the headgear 154 may be provided in a first color and a portion or an entirety of the front portion 200 may be provided in a second, different color. As shown in FIG. 9D, a transition between the front portion 200 and the rear portion 210 can include additional colors or designs, such as stripes or bands to act as a graduated transition. Moreover, either or both of the front portion 200 and the rear portion 210 can include multiple colors, patterns or textures.

FIGS. 9A-9C also illustrate possible variations in the shapes of the junctions 220. For example, the slots 370 (FIG. 4) can assume different shapes to provide one or more of the base portion 350, transition regions 352 or ends 280, 282, 290, 292 of the straps 230, 232 with different shapes. Exemplary shapes of the slots 370 can include triangular, quadrilateral (e.g., rhombus, diamond (FIG. 9C), square, trapezoid), pentagon (FIG. 9A), other polygons, round or circular (FIG. 9B), combinations of the foregoing, etc. Additional examples of alternative junctions 220 are disclosed herein with reference to FIGS. 23A-23D.

Figure 11:
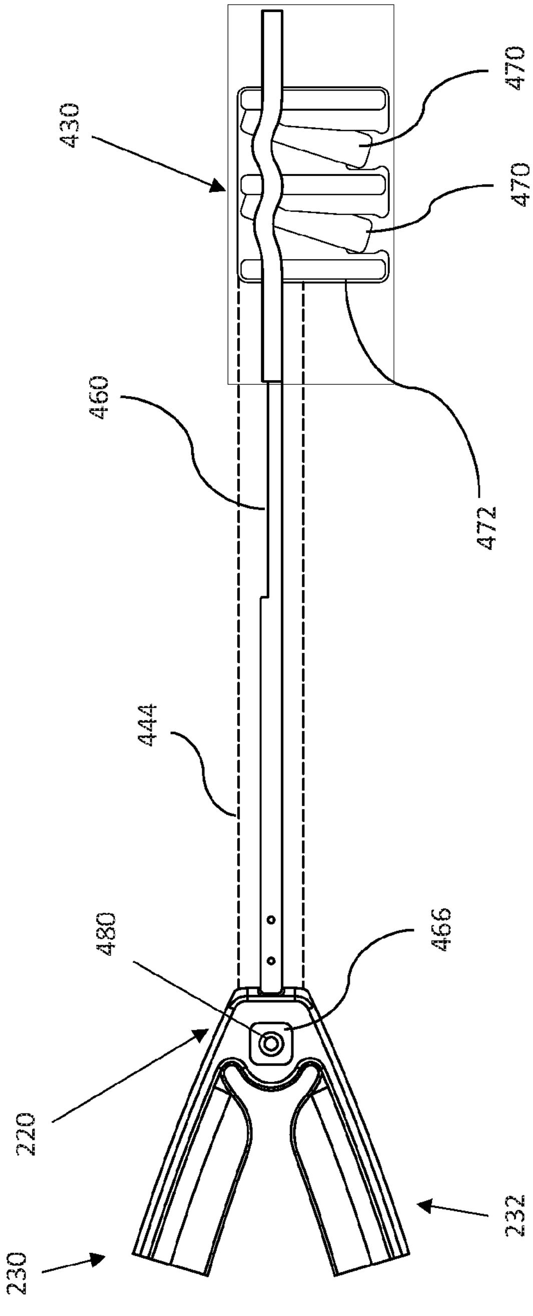
FIG. 11 illustrates a connection between an elongate plastic member of the side strap and the rear portion of the headgear.
Figure 12:
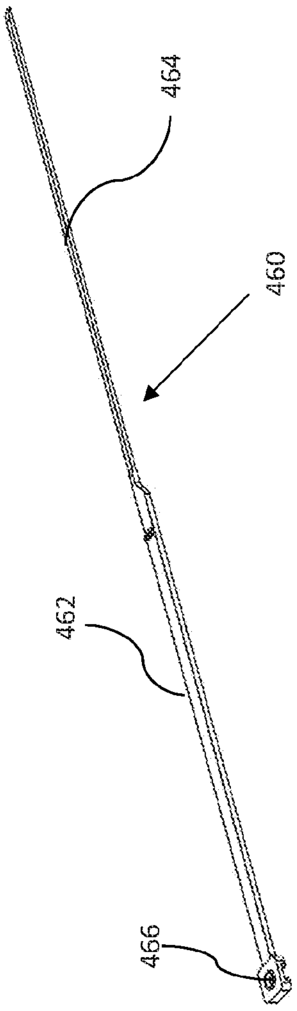
FIG. 12 is a perspective view of the elongate plastic member of the side strap.

As described above, the mask assembly 150 employs one or more directional locks 430 that provide for different resistance to different directions of movement between the mask 152 and the headgear 154. The side straps 212 provide for the variation in the closed loop perimeter length of the mask assembly 150 and provide an elastic force tending to reduce the closed loop perimeter length against the second resistance force offered by the directional lock(s) 430. In the illustrated arrangement, a directional lock 430 is located on each side of the mask assembly 150 and interacts with a portion of the associated side strap 212. As shown in FIGS. 11 and 12, the headgear 154 includes an elongate plastic member 460 that is coupled to the rear portion 210 of the headgear 154, extends along the side strap 212, and engages the directional lock 430 (FIG. 11). In the illustrated arrangement, the elongate plastic member 460 extends within the cover 440 or between the layers 260, 262 of the cover 440.

The illustrated elongate plastic member 460 includes a first portion 462 and a second portion 464. The first portion 462 is a relatively thicker portion and the second portion 464 is a relatively thinner portion. The relative difference in the thickness between the first portion 462 and the second portion 464 can be in one or both cross-sectional dimensions. However, in the illustrated arrangement, the elongate plastic member 460 has a consistent thickness and varies in width (or height in an in-use orientation) between the first portion 462 and the second portion 464. The first portion 462 can provide some rigidity to at least a portion of the side strap 212 at least relative to the cover 440 alone. The second portion 464 can interface with the directional lock 430. In the illustrated arrangement, the elongate plastic member 460 has a rectangular or generally rectangular cross-sectional shape.

As illustrated in FIG. 11, the second portion 464 of the elongate plastic member 460 engages the directional lock 430. The directional lock 430 can be any suitable arrangement to create the above-described differential resistance to different directions of relative movement between the elongate plastic member 460 and the directional lock 430. In some configurations, the directional lock 430 can include one or more lock elements 470. The lock element(s) 470 can be movable (e.g., pivotable) within a support or housing 472. The second portion 464 of the elongate plastic member 460 passes through the housing 472 and through an aperture in the lock element(s) 470. Movement of the elongate plastic member 460 relative to the directional lock 430 can move the lock element(s) 470 between a first position in which the directional lock 430 exhibits the first resistance force and a second position in which the directional lock 430 exhibits the second resistance force.

An end of the elongate plastic member 460 opposite the second portion 464 includes a hub 466. The hub 466 can facilitate connection of the elongate plastic member 460 to the rear portion 210 of the headgear 154. The hub 466 can engage the rear portion 210. In some configurations, the hub 466 or the hub 466 and an adjacent portion of the first portion 462 of the elongate plastic member 460 can be joined to the rear portion 210 with an overmolded joint, as illustrated in FIG. 11. In particular, the plastic core 270 of the rear portion 210 can be overmolded onto or over the hub 466 or the hub 466 and an adjacent portion of the first portion 462 of the elongate plastic member 460. The hub 466 can be located within the base portion 350 of the junction 222. In some configurations, a length 467 of the hub 466 can be between about 5 mm-10 mm, about 6 mm-9 mm, about 7 mm-8 mm, or about 7.5 mm.

The hub 466 can be configured to facilitate the molding of the plastic core 270 in general or the overmolding of the plastic core 270 to the elongate plastic member 460. With reference to FIGS. 13-18, the hub 466 can include an inlet or port 480 configured to receive the molten plastic material that forms the plastic core 270. In some configurations, the a diameter of the port 480 can be between about 1 mm-5 mm, 2 mm-4 mm, or about 3 mm. The hub 466 can include an interior channel or flow channel 482 that connects to the port 480 and opens to an exterior surface of the hub 466. In the illustrated arrangement, the flow channel 482 extends in a widthwise direction across an entirety of the hub 466. In some configurations, a length 481 of the flow channel 482 can be between about 1 mm-5 mm, about 2 mm-4 mm, or about 2.5 mm. In some configurations, a thickness or a height 483 of the flow channel 482 can be about 0.5 mm-3 mm, about 1 mm-2 mm, or about 1 mm. Molten plastic material received within the port 480 can pass out of the hub 466 through the flow channel 482 to create the plastic core 270.

In the illustrated arrangement, the hub 466 includes a first wall or cap 490 and a second wall or cap 492. The first cap 490 can be an exterior cap 490 located on an exterior side of the headgear 154 in use and the second cap 492 can be an interior cap 492 located on an interior side of the headgear 154 in use. The exterior cap 490 and the interior cap 492 can be formed separately or in a separated state and coupled together to form the hub 466. For example, the exterior cap 490 can be connected to the first portion 462 of the elongate plastic member 460. The interior cap 492 can be connected to the exterior cap 490 by a hinge connection 494. However, this arrangement could also be reversed.

As noted above, the exterior cap 490 and the interior cap 492 can be connected to form the hub 466. For example, the exterior cap 490 and the interior cap 492 can include cooperating connection or alignment features to facilitate the alignment or connection of the caps 490, 492. In the illustrated arrangement, the exterior cap 490 can include one or more (e.g., a pair) of alignment or connection holes 500 and the interior cap 492 can include one or more (e.g., a pair) of alignment or connection pins 502 that are received within the connection holes 500. However, this arrangement could also be reversed.

Figure 13:
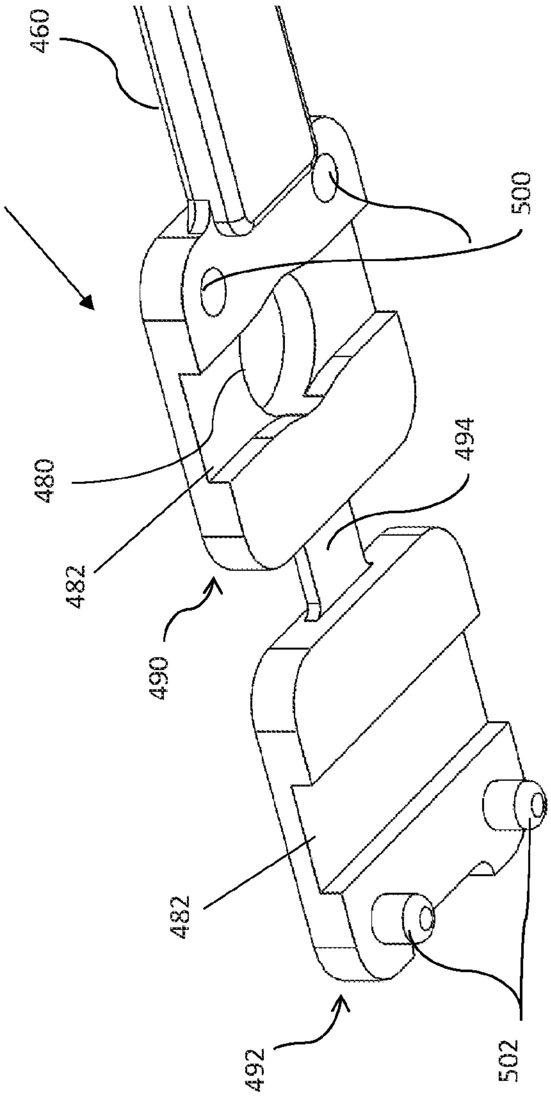
FIG. 13 is perspective view of a hub portion of the elongate plastic member of FIG. 12 with a first wall and a second wall in an open configuration.
Figure 14:
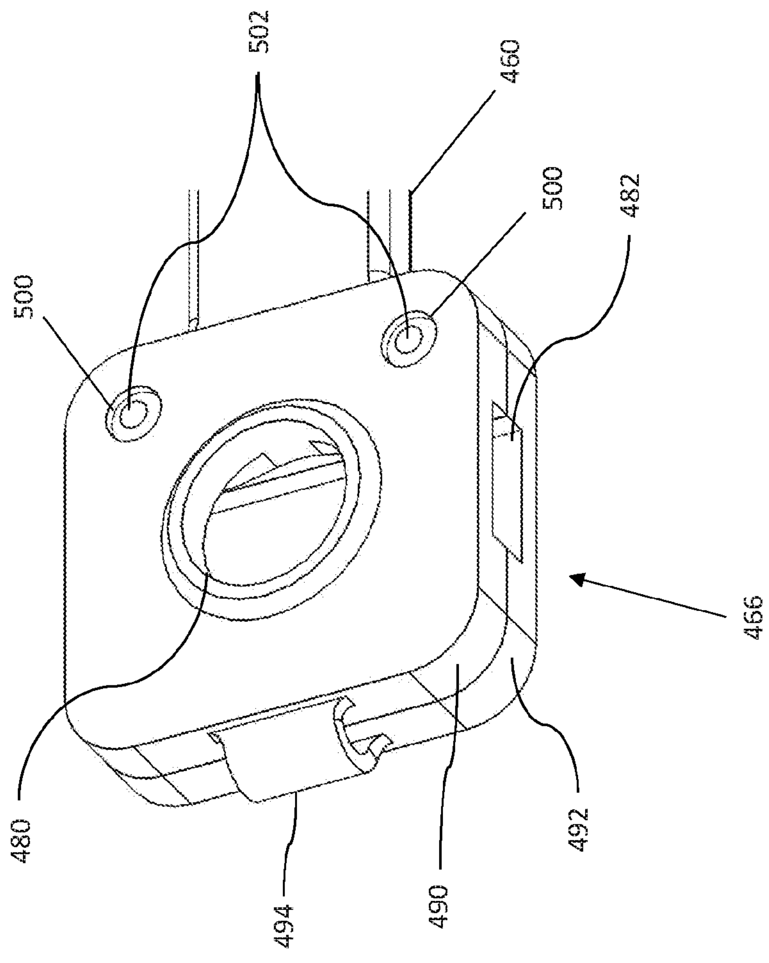
FIG. 14 is a perspective view of the hub portion of FIG. 13 in a closed configuration showing the first wall.
Figure 15:
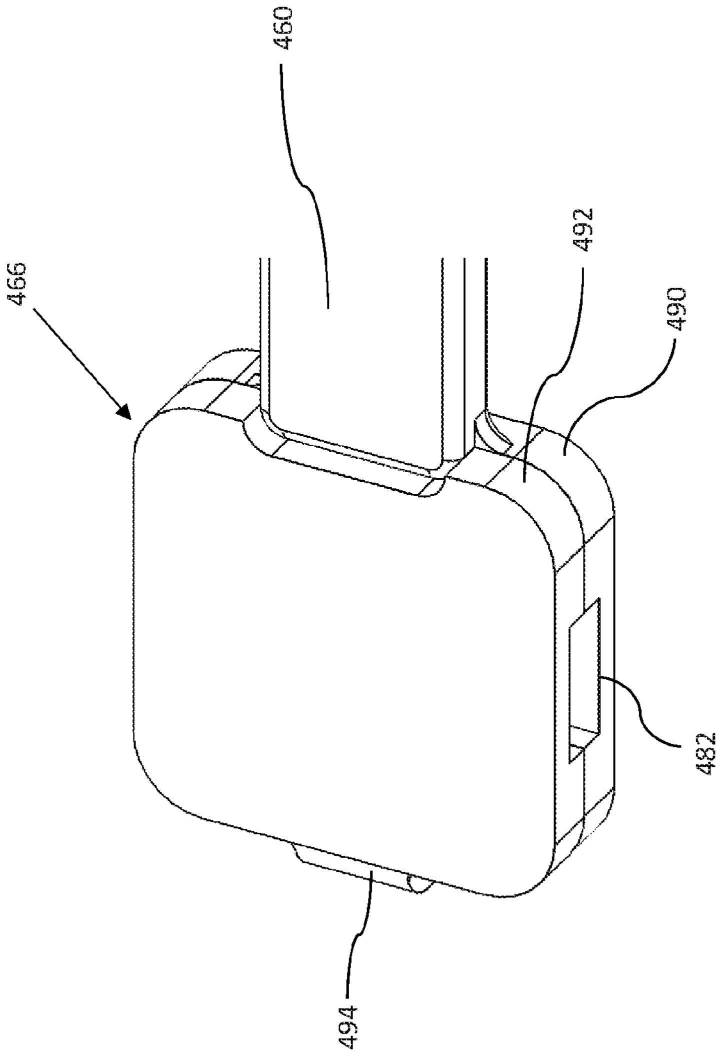
FIG. 15 is a perspective view showing the second wall of the hub portion of FIG. 14.
Figure 16:
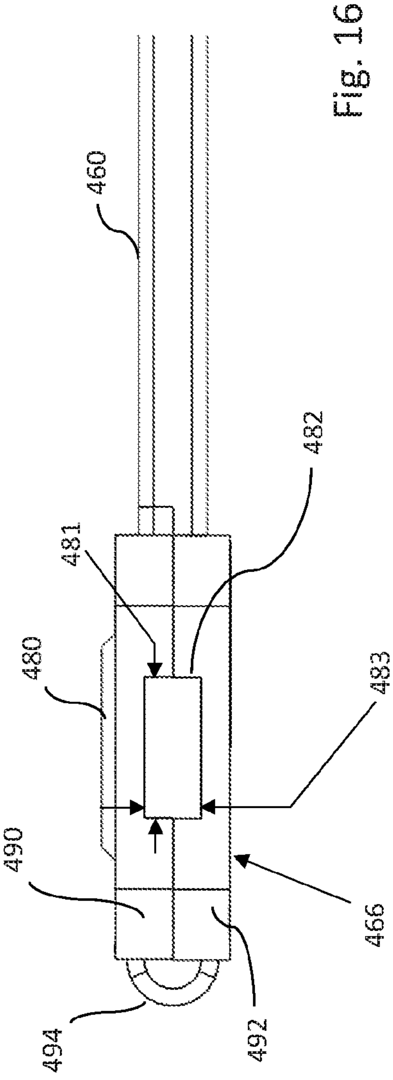
FIG. 16 is a side view of the hub portion of FIG. 14.
Figure 17:
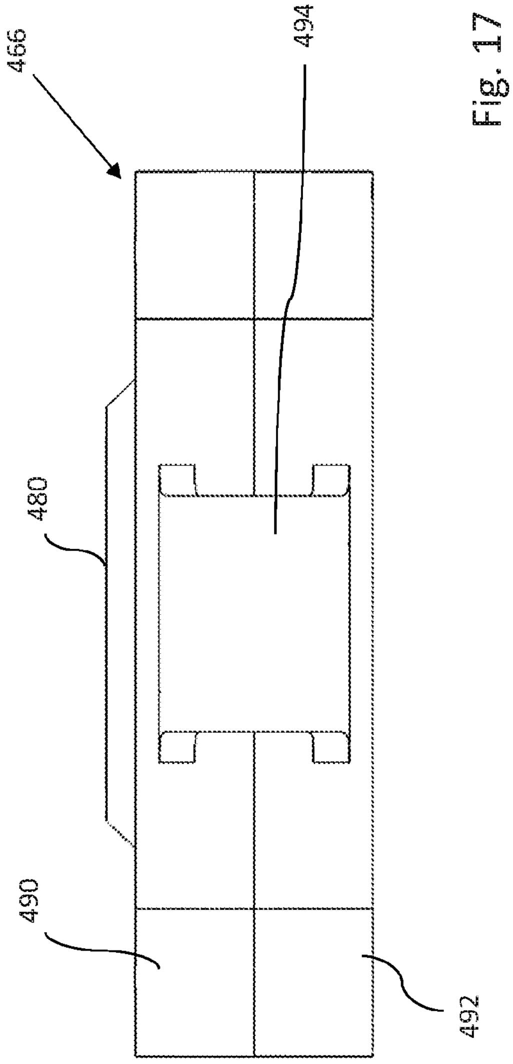
FIG. 17 is an end view of the hub portion of FIG. 14.
Figure 18:
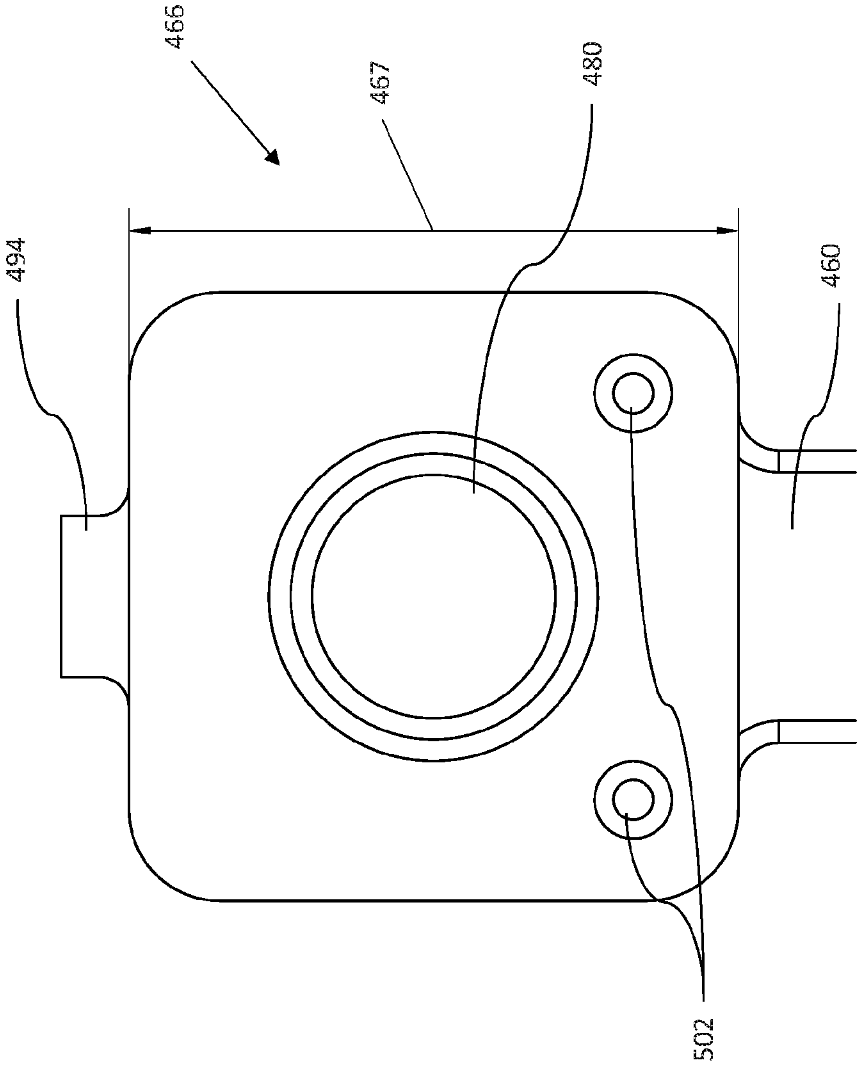
FIG. 18 is a top view of the first wall of the hub portion of FIG. 14.

The hub 466 can be molded or otherwise constructed with the exterior cap 490 and the interior cap 492 arranged in a co-planar orientation, as shown in FIG. 13. After molding, the interior cap 492 can be connected to the exterior cap 490 by flexing of the hinge 494 to create the hub 466 as illustrated in FIGS. 14-18. In the illustrated arrangement, each of the exterior cap 490 and the interior cap 492 define a portion of the depth of the flow channel 482. However, in other arrangements, one or the other of the exterior cap 490 and the interior cap 492 can define an entirety of the depth of the flow channel 482.

Figure 19:
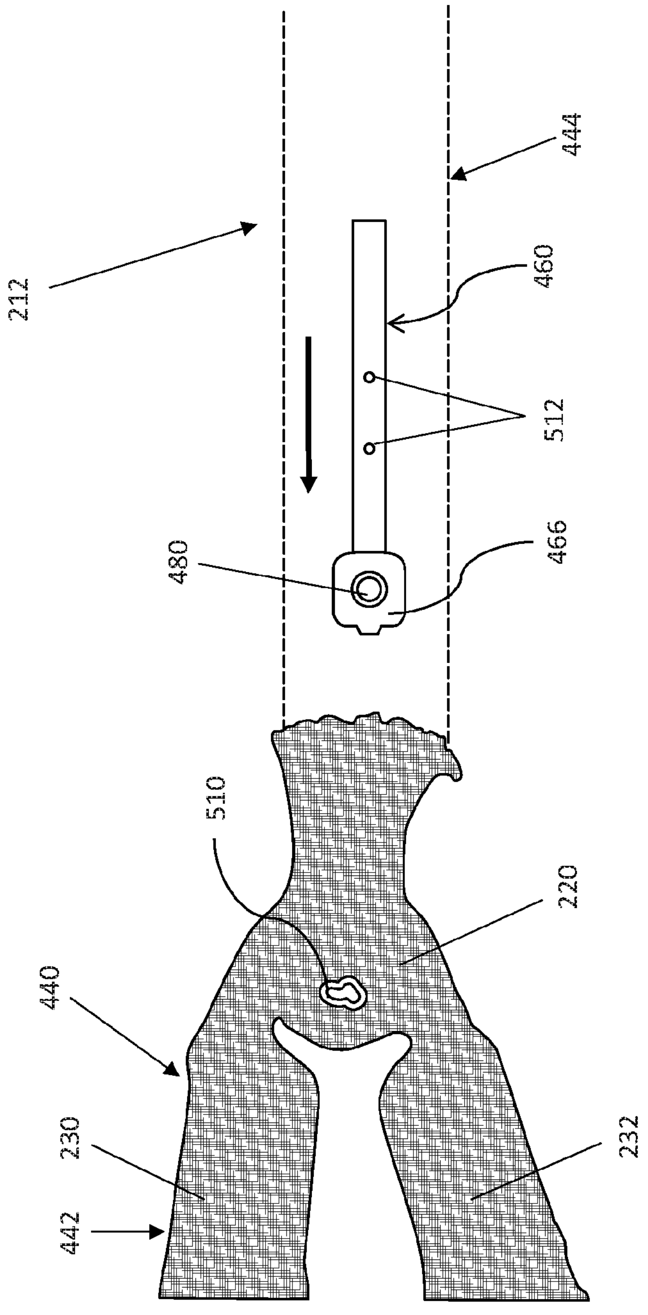
FIG. 19 illustrates insertion of the elongate plastic member into the knitted fabric cover prior to molding of the plastic core of the rear portion of the headgear arrangement.
Figure 20:
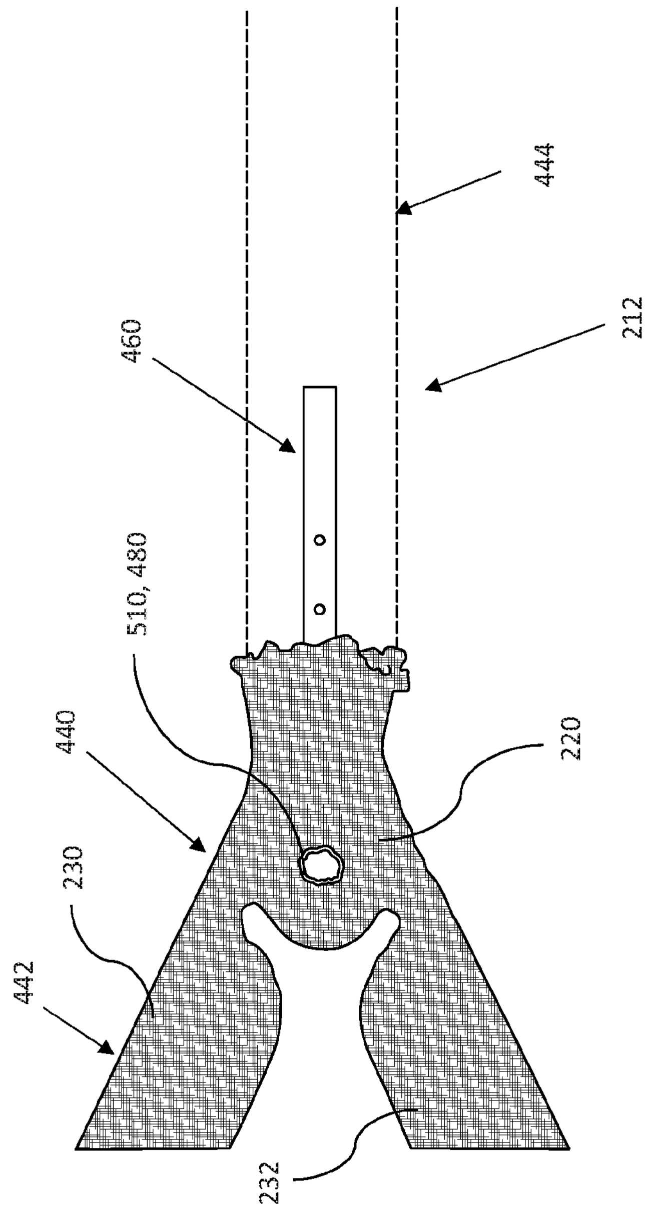
FIG. 20 illustrates the elongate plastic member within the knitted fabric cover after molding of the plastic core.

With reference to FIGS. 19 and 20, prior to overmolding with the plastic core 270, the elongate plastic member 460 is inserted into the cover 440. In FIGS. 19 and 20, a portion of the side strap 212 is cut away (shown in dashed lines) for clarity. In particular, the elongate plastic member 460 can be inserted into an open, forward end of the side strap portion 444 of the cover 440, as illustrated by the arrow in FIG. 19. The portion of the cover 440 surrounding the junction 220 of the plastic core 270 can include an aperture 510 that has a similar size and/or shape as or a slightly smaller size and/or shape than the port 480 of the hub 466. In other arrangements, the aperture 510 could be slightly larger in size and/or shape than the port 480. In other arrangements, the aperture 510 could be omitted and the molten plastic material could pass directly through the knitted cover 440 or a portion of the molding equipment (e.g., an injection needle) can pass through the knitted cover 440, such as through gaps between the yarns of the knitted cover 440. The aperture 510 can be created by the knitting process or subsequent to the knitting process. The elongate plastic member 460 is positioned within the cover 440 such that the port 480 is in alignment with the aperture 510, as shown in FIG. 20.

The cover 220 and the elongate plastic member 460 can be placed within a mold tool, such as the mold tool 420 of FIG. 8. The elongate plastic member 460 can include features to assist in locating or maintaining proper location of the elongate plastic member 460 in the mold tool 420. For example, the first portion 462 of the elongate plastic member 460 adjacent the hub 466 can include one or more alignment features or alignment holes 512 that cooperate with suitable structures (e.g., pins or projections) in the mold tool 420 to secure the elongate plastic member 460 in a desired location within the mold cavity 422.

The mold tool 420 can define an inlet or runner (not shown) to the mold cavity 422 that is aligned with the aperture 510 and port 480 of the hub 466. The molten plastic material that forms the plastic core 270 can be introduced into the mold cavity 422 through the inlet or runner, pass through the aperture 510, port 480 and flow channel 482 into the space between the layers 260, 262 of the rear portion 442 of the cover 440 to form the plastic core 270 within the cover 440. The interior cap 392, which is located opposite the port 480, can inhibit or prevent the injected molten plastic directly from the inlet or runner from penetrating through the knitted cover. FIG. 20 illustrates the rear portion 210 of the headgear with the plastic core 270 formed within and permanently connected to the rear portion 442 of the cover 440. A suitable connector (not shown) for connection to the frame 156 of the mask 152 can be coupled to the free end of the side strap portion 444 of the cover 440 by any suitable arrangement or process, such as overmolding, which could be done in the same or a different process as the formation of the plastic core 270.

Figure 21:
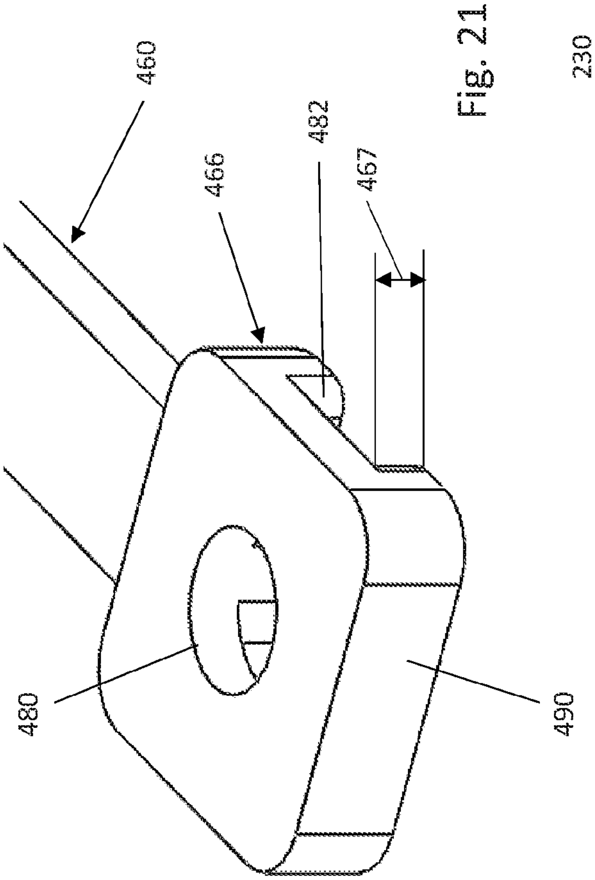
FIG. 21 is a perspective view of an alternative hub portion of the elongate plastic member of the side strap.

FIG. 21 illustrates an alternative embodiment of an elongate plastic member 460 having an alternative hub 466. In other respects, the elongate plastic member 460 can be the same as or similar to the elongate plastic member 460 described above. The hub 466 of FIG. 21 includes a single wall 490, which can generally correspond to the exterior cap 490 of the prior embodiment. It may not be necessary, at least under some conditions, to have an interior cap 492 or other structure opposite the port 480 to block or redirect the flow of molten plastic. In such situations, a simplified hub 466 arrangement can be used.

Figure 22:
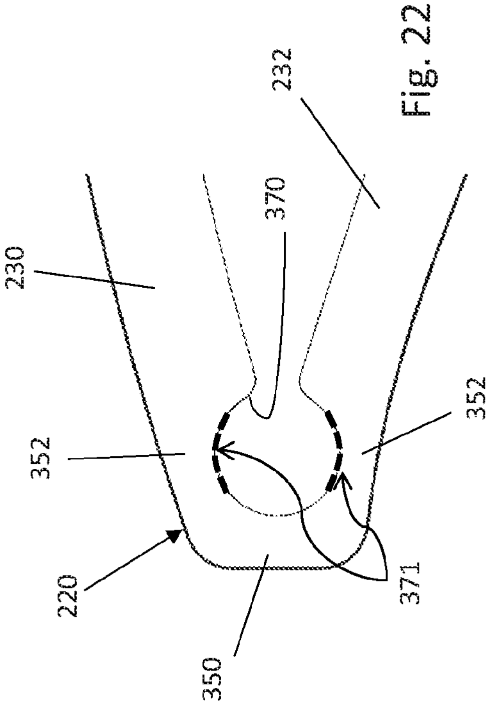
FIG. 22 is a side view of an alternative junction of the rear headgear portion.
Figure 23A:
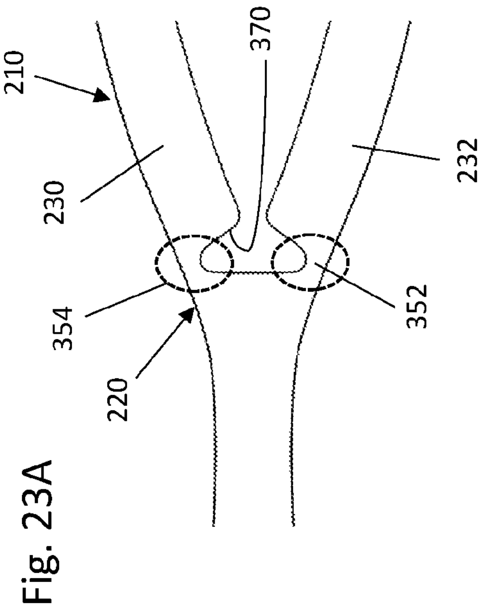
FIG. 23A-23D are side views of additional alternative junctions of the rear headgear portion.
Figure 23B:
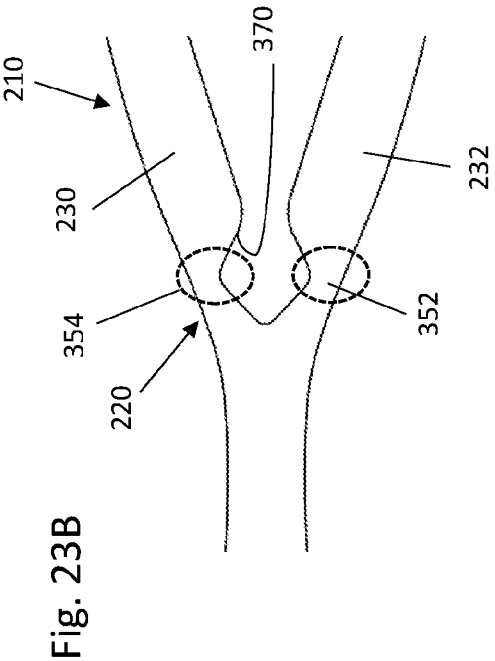
Figure 23C:
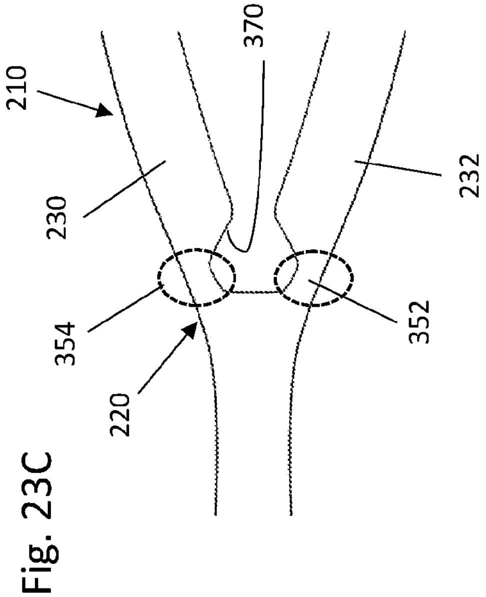
Figure 23D:
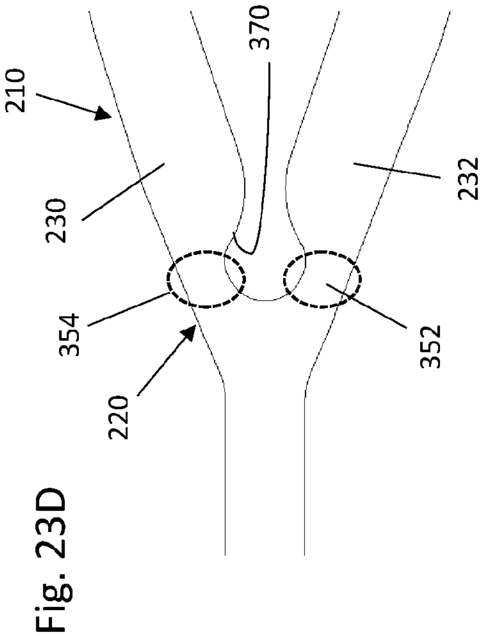

FIG. 22 illustrates an alternative junction 220, which includes a single, circular slot 370. The circular slot 370 forms a transition region 352 between the base portion 350 of the junction 220 and each of the upper strap 230 and the lower strap 232. In the illustrated configuration, the circular slot 370 can have rounded edges 371 that form the transition regions 352. The transition regions 352 can provide the rear portion 210 of the headgear 154 with the same or similar adjustment characteristics as the embodiment described above.

FIGS. 23A-23D illustrate yet additional alternative junctions 220, which can also provide the same or similar adjustment characteristics as the embodiment described above. The junction 220 of FIG. 23A includes a generally triangular-shaped slot 370, which creates a transition region 352 and a flex region 354 between the base portion 350 of the junction 220 and each of the upper strap 230 and the lower strap 232. The junction 220 of FIG. 23B includes a generally diamond-shaped slot 370, which creates a transition region 352 and a flex region 354 between the base portion 350 of the junction 220 and each of the upper strap 230 and the lower strap 232. The junction 220 of FIG. 23C includes a generally pentagon-shaped slot 370, which creates a transition region 352 and a flex region 354 between the base portion 350 of the junction 220 and each of the upper strap 230 and the lower strap 232. The junction 220 of FIG. 23D includes a generally circular slot 370, which creates a transition region 352 and a flex region 354 between the base portion 350 of the junction 220 and each of the upper strap 230 and the lower strap 232. The junction 220 of FIG. 23*d* has a gentler transition between the transition regions 352 and the straps 230, 232.

Figure 24:
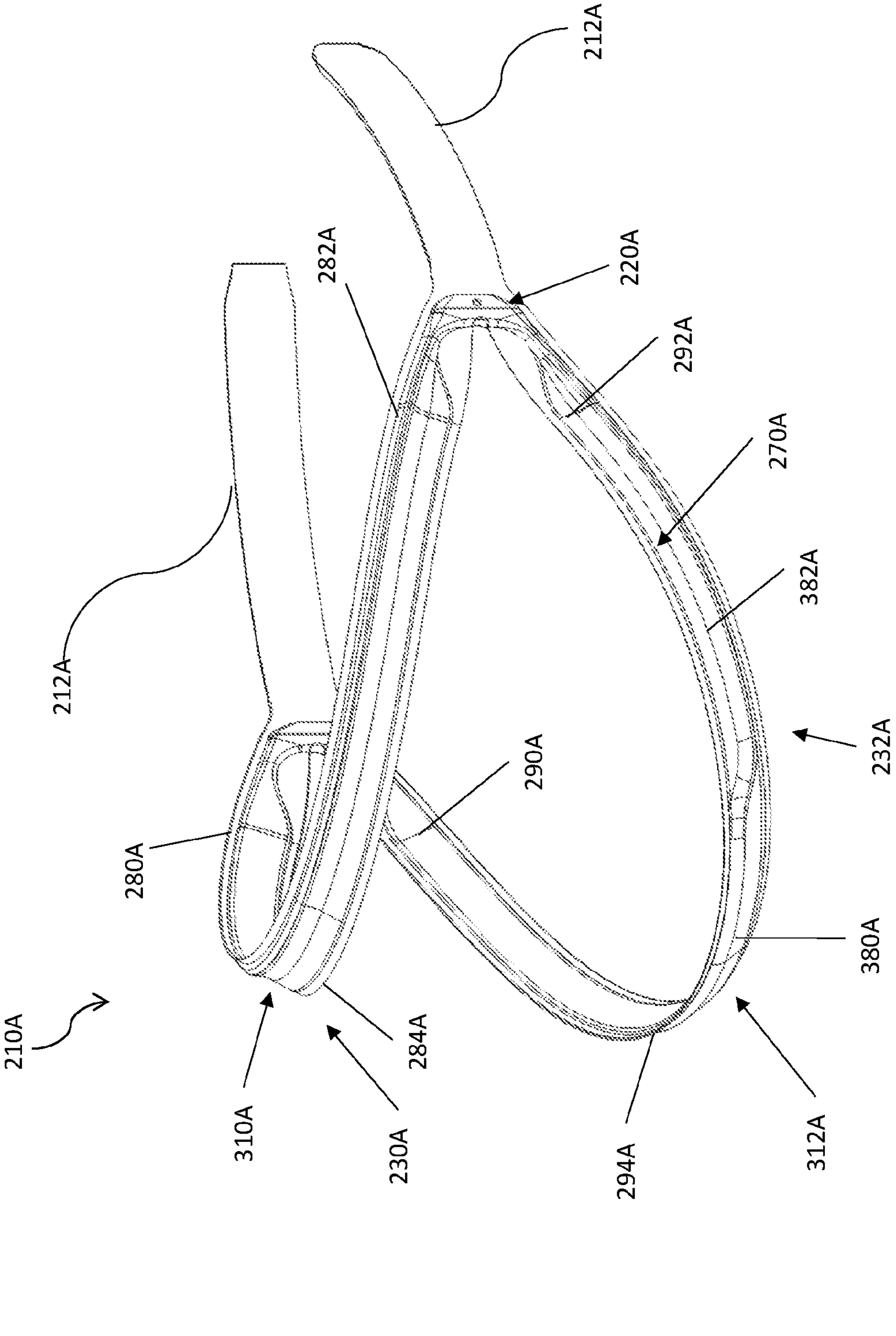
FIG. 24 is a perspective view of an alternative configuration of the rear portion of the headgear arrangement.
Figure 25:
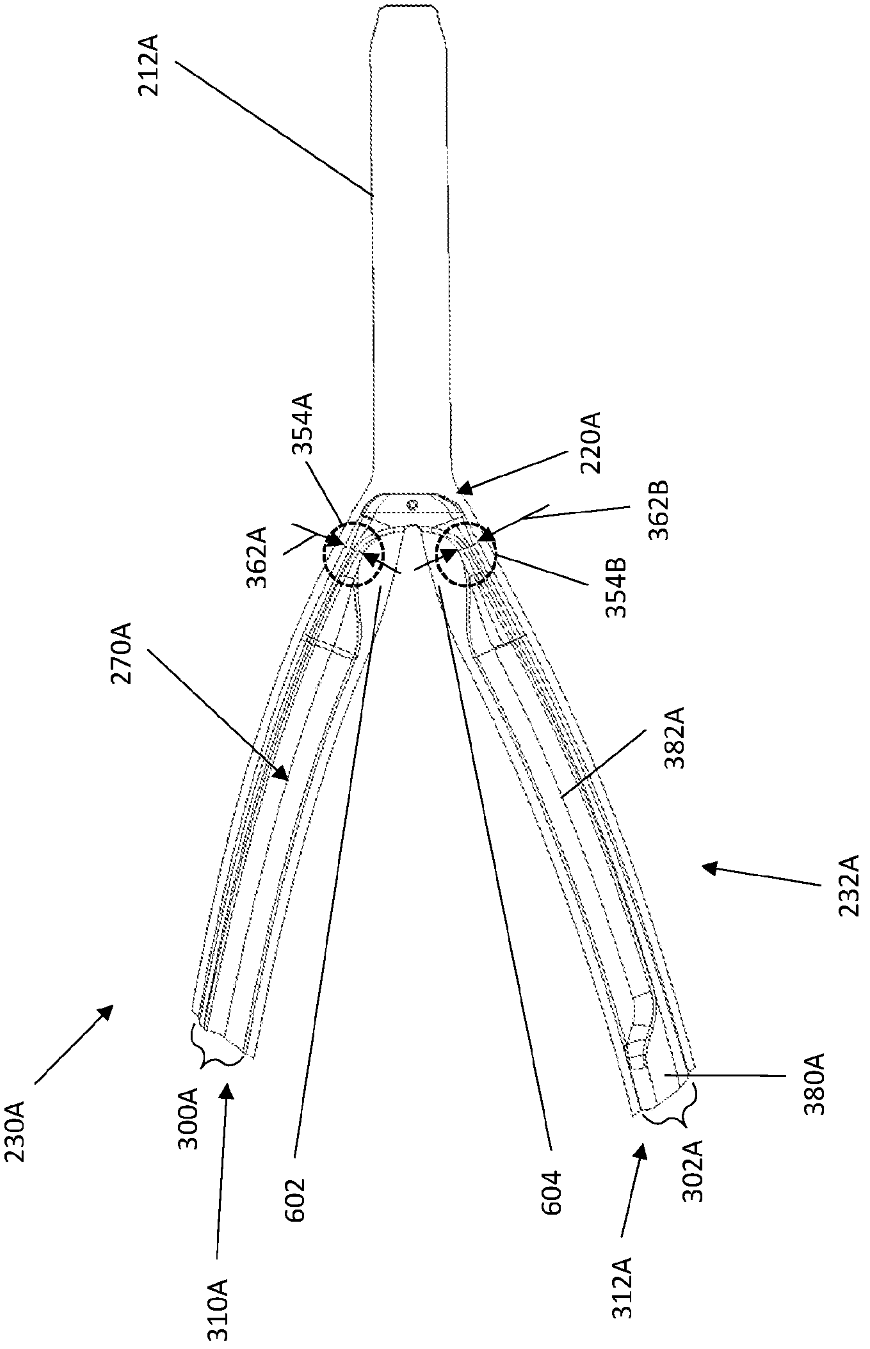
FIG. 25 is a side view of the rear portion of the headgear arrangement of FIG. 24.
Figure 26:
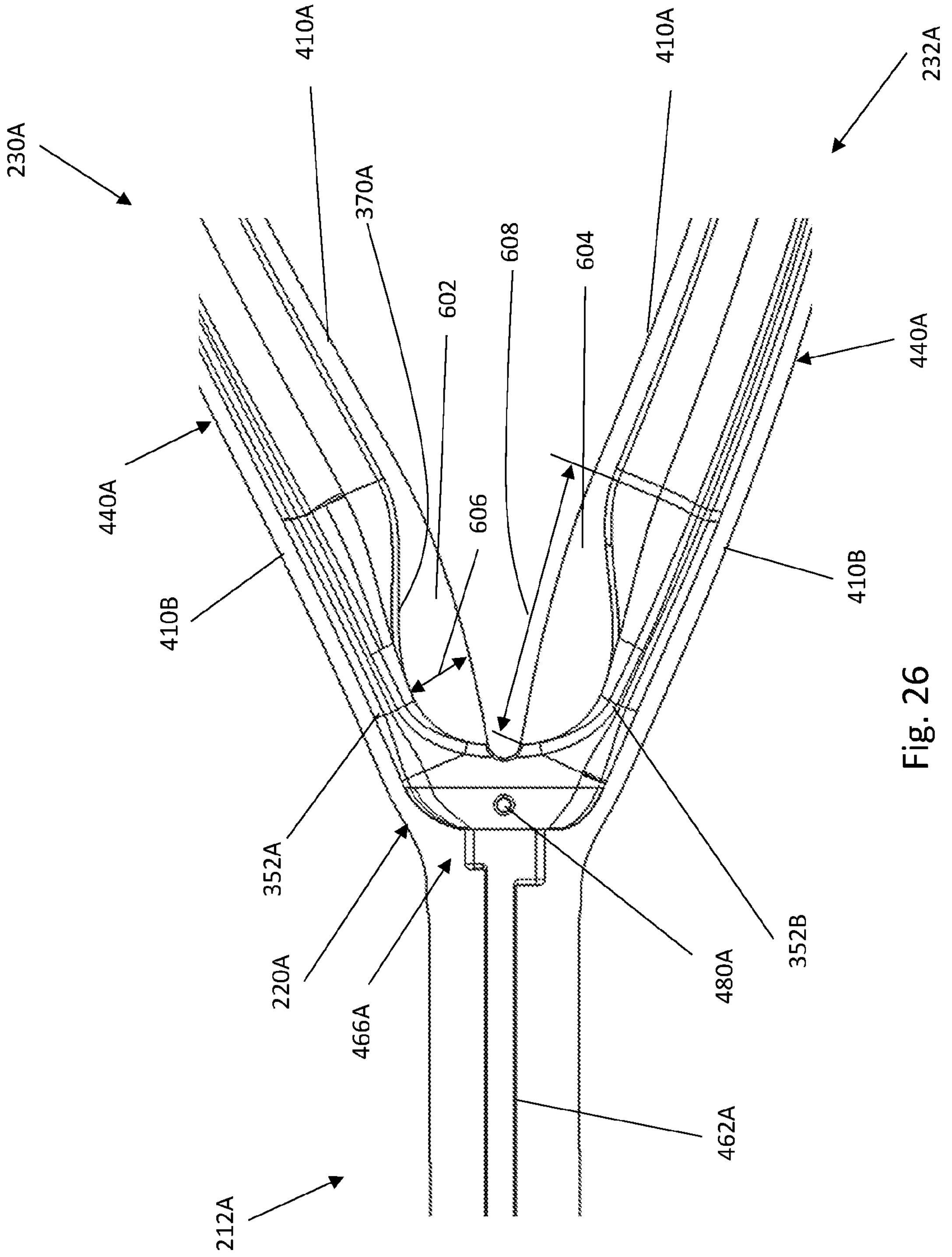
FIG. 26 is an enlarged side view showing a junction between an upper strap, a lower strap, and a side strap of the rear portion of FIG. 24.

Another configuration of a rear portion 210A of the headgear 154 is illustrated in FIGS. 24-26. FIGS. 24-26 show a configuration of the rear portion 210A that is similar to the rear portion 210 described with reference to FIGS. 2-20 and can have similar features. Reference numerals of the same, substantially the same, or corresponding features may share the same first three digits. Any component disclosed in any configuration in this specification can be used in any other configuration.

As noted above, at least the rear portion 210A can be constructed as a molded composite structure. In the illustrated arrangement, as shown in FIGS. 24-26, the rear portion 210A, including the upper strap 230A, the lower strap 232A and the junctions 220A, can be a molded composite structure having a fabric cover 440A, which can include at least one fabric layer (e.g., two fabric layers), with a plastic core 270A located within the fabric cover 440A. In FIGS. 24-26, the inner plastic core 270A and the outer fabric cover 440A are shown in solid lines, but it is understood that the plastic core 270A is internal to the fabric cover 440A—as in the prior configurations. The rear portion 210A can be formed as a unitary structure by the application of molten plastic into the space within the fabric cover 440A within a mold and allowing the molten plastic to harden to form the plastic core 270A in a shape corresponding to the shape of the mold cavity. The two fabric layers of the fabric cover 440A can be separate from one another and joined via the plastic core 270A or can be connected (e.g., a tubular structure that surrounds the plastic core 270A). The composite structure of the rear portion 210A is discussed in further detail below.

In the illustrated configuration, the plastic core 270A can be molded in a three-dimensional shape using, for example, a preformed contoured mold tool that forms the three-dimensional plastic core 270A with curves configured to approximate or conform to the shape of a user's head. This three-dimensional tool allows the plastic core 270A to be molded in a three-dimensional shape such that the different portions of the rear portion 210A are formed continuous with one another. For example, the upper and lower straps 230A, 232A are continuous rather than being formed in two or more pieces that need to be connected or combined. The continuous straps 230A, 232A allows the rear portion 210A to have smooth continuous surfaces such that the rear portion 210A can be more comfortable in use. In some configurations, one or more of the plurality of straps 212A, 230A, 232A can be configured to be inelastic such that the strap(s) 212A, 230A, 232A has no or limited ability to stretch or flex. In some configurations, the user-contacting surfaces of the rear portion 210A can have flush surfaces that have little to no variation in thickness for increased comfort for the user.

In some configurations, the upper strap 230A and the lower strap 232A can have different lengths and/or widths from one another in order to better accommodate a typical user's head shape and/or facilitate proper location of the straps 230A, 232A on the user's head. As noted above and shown in FIGS. 24 and 25, the upper strap 230A can include the first length or the upper strap length 284A that can be different than second length or the lower strap length 294A of the lower strap 232A. In the illustrated arrangement, the lower strap length 294A may be greater than the upper strap length 284A. In some configurations, the lower strap length 294A can be between about 150 mm-350 mm, between about 175 mm-325 mm, between about 200 mm-300 mm, between about 225 mm-275 mm, or about 254 mm. In some configurations, the upper strap length 284A can be between about 140 mm-340 mm, between about 160 mm-320 mm, between about 180 m-300 mm, between about 200 mm-280 mm, between about 220 mm-260 mm, or about 241 mm. In some configurations, a ratio of the lower strap length 294A to the upper strap length 284A can be between about 1.0-1.3, between about 1.1-1.2, or about 1.054. In other configurations, the upper strap length 284A can be greater than the lower strap length 294A or the two lengths 284A, 294A can be equal or substantially equal.

In some configurations, the width 300A of the upper strap 230A and the width 302A of the lower strap 232A can be equal or substantially equal. In some configurations, the widths 300A, 302A can be between about 10 mm-20 mm, between about 12 mm-18 mm, between about 14 mm-18 mm, or about 14 mm. These widths 300A, 302A can be the minimum widths, maximum widths or the average widths of the straps 230A, 232A. However, in other configurations, the widths 300A, 302A of the straps 230A, 232A can be different from one another. That is, the width 300A of the upper strap 230A can be smaller than or larger than the width 302A of the lower strap 232A.

In some configurations, the rear portion 210A can include different sizes to accommodate users with different head circumferences. For example, the rear portion 210A can include two or more of the following sizes: extra-small (XS), small (S), medium (M), large (L), and extra-large (XL). The lengths and/or widths of the upper and lower straps 230A, 232A of an extra-large rear portion 210A may be greater than the lengths and/or widths of the upper and lower straps 230A, 232A of an extra-small rear portion.

In some configurations, the upper strap 230A and/or the lower strap 232A can include a relatively stiffer or reinforced portion (i.e., the main strap portion 380A) that can have a greater thickness than adjacent portions of the strap 230A, 232A. In these configurations, the upper strap 230A and/or the lower strap 232A can include the one or more relatively less stiff portions (i.e., the flange portions 382A) that can have a lesser thickness than the main strap portion 380A. As shown in FIGS. 24 and 25, the central portion 312A of the lower strap 232A can be defined by a main strap portion 380A. The flange portions 382A can be positioned on either side of the main strap portion 380A. The length of the main strap portion 380A can be between about 40 mm-60 mm, between about 45 mm-55 mm, or about 53 mm. In some configurations, only one of the straps 230A, 232A includes the relatively stiffer or reinforced portion (i.e., the main strap portion 380A). In the illustrated configuration, only the lower strap 232A includes the relatively stiffer or reinforced portion (i.e., the main strap portion 380A). This configuration provides a tactile and visual orientation feature that assists a user in determining the correct orientation of the rear portion 210A in use. However, in other configurations the arrangement could be reversed such that only the upper strap 230A includes the relatively stiffer or reinforced portion (i.e., the main strap portion 380A).

FIG. 26 shows an enlarged view of the junction 220A between the upper strap 230A, lower strap 232A, and the side straps 212A. In the illustrated configuration, the junction 220A can include a substantially U-shape slot 370A defined by the plastic core 270A, which creates a transition region 352A, 352B and a flex region 354A, 354B (FIG. 25) between the base portion 350A of the junction 220A and one of the upper strap 230A and the lower strap 232A. In some configurations, a width 362A of the first transition region 352A of the upper strap 230A can be different than a width 362B of the transition region 352B of the lower strap 232A. For example, the width 362A of the first transition region 352A may be less than or greater than the width 362B of the second transition region 352B. In some configurations, the relative widths of the transition regions 352A, 352B are related or proportional to the relative volumes of the respective straps 230A, 232A defined by the plastic core 270A, which differences may relate to differences in length and/or thickness. That is, the strap 230A, 232A with the greater volume of plastic material may have the transition region 352A, 352B of greater width 362A, 362B. In some configurations, the width 362A of the first transition region 352A may be about 3.5 mm and the width 362B of the second transition region 352B may be about 4 mm. During manufacturing, the greater width 362B of the second transition region 352B can facilitate a greater flow of molten plastic material from the port 480A that may be needed to form the longer lower strap 232A with the main strap portion 380A.

In some configurations, as shown in FIG. 26, the knitted cover 440A can include a width that is constant or near constant through the length of the knitted cover 440A. The constant or near constant width of the knitted cover 440A can reduce the time taken in the knitting process. Moreover, as previously described, the transition regions 352A, 352B of the plastic core 270A can have a reduced width 362A, 362B (FIG. 25) relative to the base portion 350A of the junction 220A and/or the upper and/or lower straps 230A, 232A. In some configurations, the knitted cover 440A can have a slight taper at the transition regions 352A, 352B such that the knitted cover 440A has smooth curves along the transition regions 352A, 352B. For example, the decrease of the width of the knitted cover 440A from the widest portion of the knitted cover 440A to the narrowest portion can be between about 10%-30% or between about 15%-25%. During manufacturing, the width of the knitted cover 440A can be tapered by tightening the knit of the knitted cover 440A towards the junction 220A where the upper and lower straps 230A, 232A meet in order to, for example, minimize the length of the knitted cover 440A at the base of the junction 220A.

In some configurations, the knitted cover 440A can form a fabric flap 602, 604 adjacent each of the transition regions 352A, 352B. Each fabric flap 602, 604 is a region of the knitted cover 440A that is unsupported by the plastic core 270A and is substantial in width relative to the width of the corresponding strap 230A, 232A. In some configurations, the cover 440A can include inner protruding edges 410A (i.e., the lower edge of the upper strap 230A and the upper edge of the lower strap 232A) and outer protruding edges 410B (i.e., the upper edge of the upper strap 230A and the lower edge of the lower strap 232A). In some configurations, the fabric flaps 602, 604 can be formed using the same or similar process as the protruding edges 410A, 410B. In some configurations, the fabric flap 602, 604 can be continuous with the inner protruding edges 410A. In some configurations, a width 606 of the fabric flap 602, 604 can be greater than the width of the protruding edges 410A, 410B. Preferably, each fabric flap 602, 604 is significantly wider than either one of the protruding edges 410A, 410B and, in some configurations, may be at least twice as wide as either one of the protruding edges 410A, 410B. In some configurations, each fabric flap 602, 604 is at least about one-quarter, at least about one-third or at least about one-half of the width of the corresponding strap 230A, 232A at either a location corresponding to the fabric flap 602, 604 or at a maximum width of the corresponding strap 230A, 232A. For example, the width 606 of the fabric flaps 602, 604 can be between about 2 mm-7 mm, between about 3 mm-6 mm, between about 4 mm-6 mm, or about 5.8 mm. In some configurations, the fabric flap 602, 604 can have a length 608 (e.g., between the junction 220 and the protruding edge 410) of between about 15 mm-40 mm, between about 20 mm-35 mm, between about 25 mm-30 mm, or about 26 mm. In some configurations the width 606 of the fabric flap 602, 604 can vary along the length 608 of the fabric flap 602, 604 such that the knitted cover 440A smoothly transitions from one portion to another (e.g., from the fabric flap 602, 604 to the protruding edges 410A).

Figure 27:
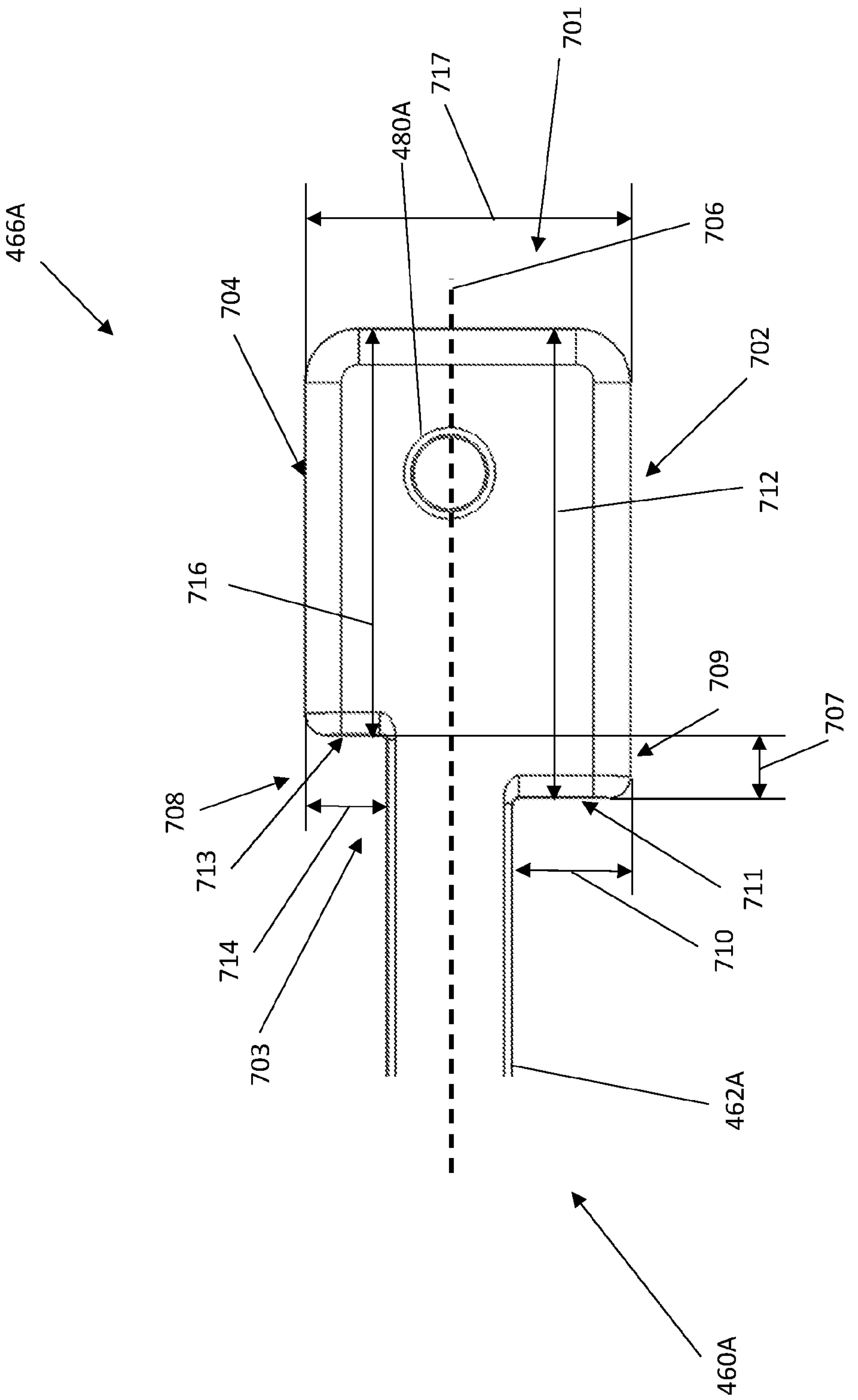
FIG. 27 is a side view of an alternative configuration of a hub portion.
Figure 28:
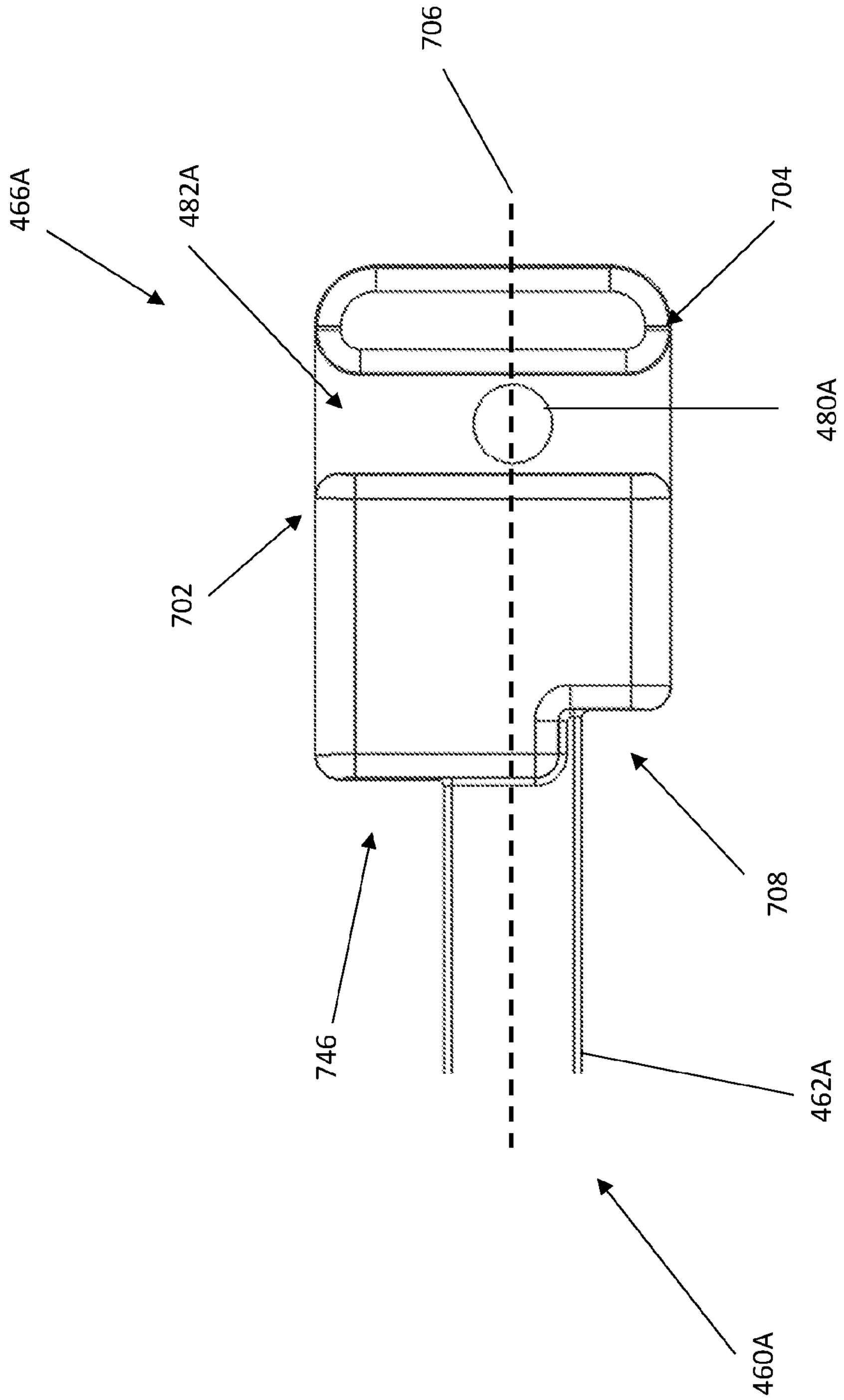
FIG. 28 is a side view of the hub portion of FIG. 27, wherein this side is opposite the side of FIG. 27.
Figure 29:
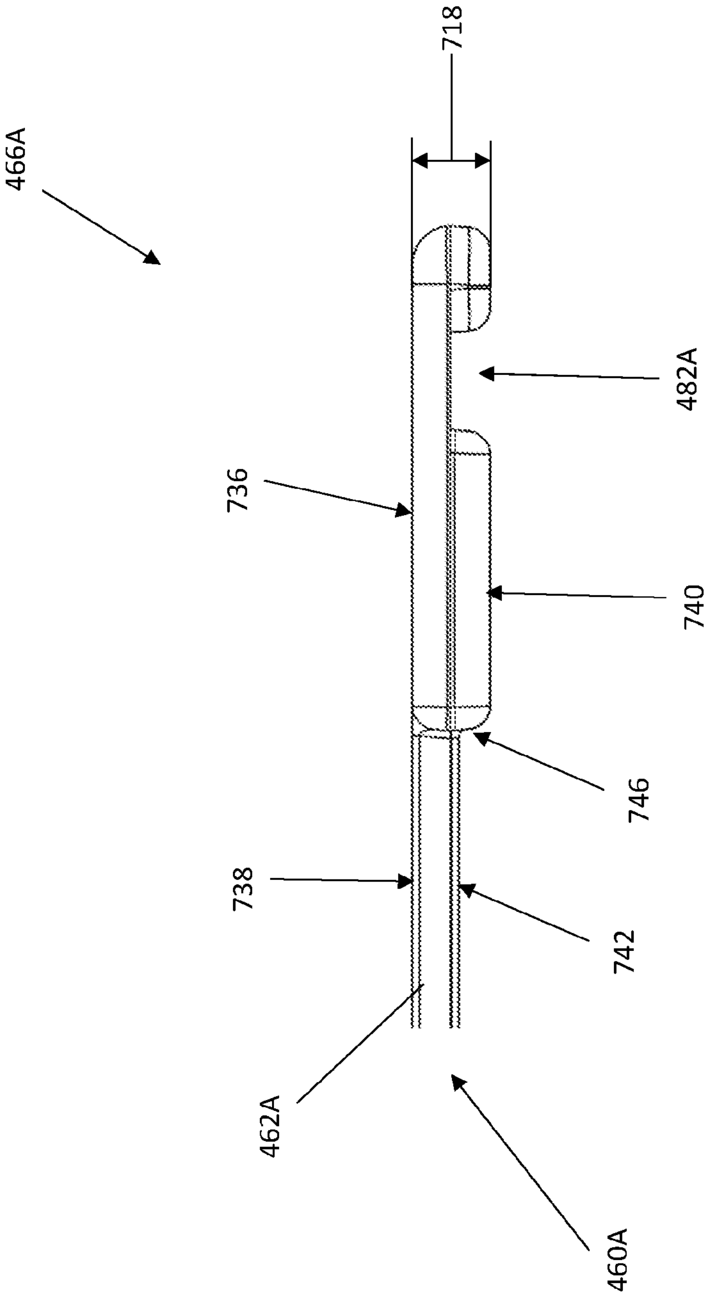
FIG. 29 is a side view of the hub portion of FIG. 27, wherein this side is normal to the sides of FIGS. 27 and 28.

Another configuration of a hub 466A is illustrated in FIGS. 27-29. FIGS. 27-29 show a configuration of the hub 466A that is similar to the hub 466 described with reference to FIGS. 11-21 and can have similar features. Reference numerals of the same, substantially the same, or corresponding features may share the same first three digits. Any component disclosed in any configuration in this specification can be used in any other configuration.

With reference to FIGS. 27-29, the hub 466A can comprise a substantially rectangular shape. For example, a length 712, 716 of the hub 466A can be greater than a width 717 of the hub 466A. In some configurations, the length 712, 716 of the hub 466A can be between about 10 mm-15 mm, between about 12 mm-14 mm, or about 13 mm. In some configurations, the width 717 of the hub 466A can be between about 5 mm-10 mm, between about 7 mm-8 mm, or about 9 mm. In some configurations, a thickness 718 of the hub 466A can be between about 1 mm-5 mm, between about 2 mm-4 mm, or about 2 mm. In some configurations, a diameter of the port 480A can be between about 1 mm-5 mm, between about 2 mm-4 mm, or about 2 mm. As shown in the illustrated configurations, the port 480A can be positioned on the hub 466A such that the port 480A aligns with a position at or near the center of the junction 220A (FIG. 26). In some configurations, the port 480 can be positioned at other locations on the hub 466.

In some configurations, the hub 466A can comprise a first side portion 702 and a second side portion 704. The hub 466A can be used in any orientation of the product as used. In some configurations, the first side portion 702 of the hub 466A can be oriented relatively downward or on the same side as the lower strap 232A and the second side portion 702 of the hub 466A can be oriented relatively upward or on the same side as the upper strap 234A or vice versa. In other words, the first side portion 702 can be on one side of a longitudinal axis 706 of the elongate plastic member 460A and the second side portion 704 can be on the other side. In some configurations, the vertical orientation of the hub 466A (relative to the orientation shown in FIGS. 27 and 28) can be flipped or reversed from one side of the headgear 154 to the other. Such an arrangement allows a single elongate plastic member 460A, including the hub 466A, to be used on each side of the headgear 154, which reduces manufacturing and storage costs and simplifies the manufacturing process relative to a design that uses different hubs 466A for each side of the headgear 154.

In some configurations, the hub 466A can be asymmetrical relative to one or more axes or in one or more directions of the hub 466A. For example, the hub 466A can be asymmetrical along or about the longitudinal axis 706 of the elongate plastic member 460A. For example, the first and second side portions 702, 704 can have respective widths 710, 712 and lengths 714, 716. The first width 710 and first length 712 of the first side portion 702 can be greater than the second width 714 and the second length 716 of the second side portion 704. Alternatively, the second width 714 and second length 716 can be greater than, the same, or substantially the same as the first width 710 and the first length 712. In some configurations, the first width 710 can be between about 2 mm-5 mm, between about 3 mm-4 mm, or about 3.25 mm. In some configurations, the first length 712 can be between about 10 mm-15 mm, between about 12 mm-13 mm, or about 13 mm. In some configurations, the second width 714 can be between about 1 mm-4 mm, between about 2 mm-3 mm, or about 2.25 mm. In some configurations, the second length 716 can be between about 10 mm-15 mm, between about 11 mm-14 mm, or about 11.25 mm. In some configurations, the hub can be asymmetrical about a vertical axis of the hub 466A that extends through a centre of the length 712, 716 of the first or second side portion 702, 704. In some configurations, the hub can be asymmetrical about both the longitudinal axis 706 of the first portion 462A of the elongate plastic member 460A and the vertical axis of the hub 466A.

As shown in the illustrated configurations, the second side portion 704 can include an orientation notch 708 and/or the first side portion 702 can include an orientation key 709. In some configurations, the hub 466A can include a first end 701 and a second end 703 that can be integral with or attached to the first portion 462A of the elongate plastic member 460A. In the illustrated configuration, the first end 701 of the hub 466A can be continuous along each of the first and second side portions 702, 704. Also, the second end 703 of the hub 466A can include an offset 707 such that a second end 711 of the first side portion 702 is offset from a second end 713 of the second side portion 704. In some configurations, the second end 703 of the hub 466A can be continuous while the first end of the 701 of the hub 466A can include an offset. In some configurations, both the ends 701, 703 can be continuous or include and offset. During manufacturing, the hub 466A and the first portion 462A of the elongate plastic member 460A can be placed into a cavity of the three-dimensional mold tool described above, or the mold tool 420 described in relation to FIG. 8, for overmolding the hub 466A to the plastic core 270A. This overmolding process can be the same or similar to the overmolding process described elsewhere in this disclosure. The orientation notch 708, the orientation key 709 and/or the asymmetry of the hub 466A can reduce the risk of the elongate plastic member 460A being incorrectly assembled. For example, the asymmetry of the hub 466A can prevent the incorrect orientation with respect to the two orientations shown in FIGS. 27 and 28. In addition, as discussed above, the orientation of the hub 466A could be different on each side of the headgear 154.

Another configuration of the side straps 212A of the headgear 154 is illustrated in FIGS. 30A-32. The difference between this configuration of side straps 212A and the previously described configurations is the addition of a support structure 728, which is further described below.

In some configurations, the support structure 728 can be fixed to the rear portion 210A of the headgear 154. For example, with reference to FIGS. 30A-30D, the elongate plastic member 460A can be engaged with, supported by or at least partially constrained by the support structure 728. For example, the support structure 728 can comprise rigid or semi-rigid material (e.g., plastic) and have an elongate body with a channel extending through its length. The elongate plastic member 460A can pass through the channel and the support structure 728 can constrain at least a part of the elongate plastic member 460A. In some configurations, the support structure 728 can include a medial collar 724 and a lateral collar 720. The medial collar 724 can be positioned on the medial side of the support structure 728 and the lateral collar 720 can be positioned on the lateral side of the support structure 728 when worn. The user can move the elongate plastic member 460A within the support structure 728 to change a length of the side strap 212A, as further described below.

In some configurations, the knitted cover 440A can enclose the support structure 728. In some configurations, the knitted cover 440A can cover a portion (e.g., one side) of the elongate plastic member 460A and/or the support structure 728. In some configurations, the support structure 728 can comprise a rectangular cross-section, an exterior side 730 facing away from the user's face, and an interior side (not shown) facing towards the user's face. The interior side of the support structure 728 can have a solid wall while the exterior side 730 of the support structure 728 can have an opening 734 extending part of the length of the support structure 728. For example, the opening 734 can extend between a length between the medial and lateral collars 720, 724.

With reference to FIGS. 28-30D, in some configurations, an exterior surface 736 of the hub 466A can be aligned in a thickness direction or continuous with an exterior surface 738 of the first portion 462A of the elongate plastic member 460A. In some configurations, as shown in FIG. 29, an interior surface 740 of the hub 466A can be offset from an interior surface 742 of the first portion 462A of the elongate plastic member 460A. The offset between the two interior surfaces 740, 742 can create a step in the height, which can create an abutment wall 746 that the support structure 728 can abut, as further described below. In some configurations, at least a portion of the hub 466A is not covered by the overmolded rear portion 210. For example, as shown in FIG. 26, a lateral portion of the hub 466A can be overmolded with the junction 220A such that the abutment wall 746 can extend beyond a medial wall of junction 220A. In some configurations, the exterior surfaces 736, 738 can be offset from one another while the interior surfaces 740, 742 can be continuous with one another. In some configurations, both the exterior surfaces 736, 738 and the interior surfaces 740, 742 can be offset from one another or continuous with one another.

As described above and with reference to FIGS. 31 and 32, the elongate plastic member 460A can include the relatively wider first portion 462A and the relatively narrower second portion 464A. In some configurations, the first portion 462A can have a width of about 3.5 mm while the second portion 464A can have a width of about 0.86 mm. In some configurations, the elongate plastic member 460A can include a transition region 748 between the first and second portions 462A, 464A in which the width of the elongate plastic member 460A tapers from the wider first portion 462A to the narrower second portion 464A. In one example, a length of the first portion 462A including the transition region 748 can be about 100 mm and a length of the second portion 464A can about 95 mm. These lengths however may be variable depending on other features of the directional locks 430.

Figure 30A:
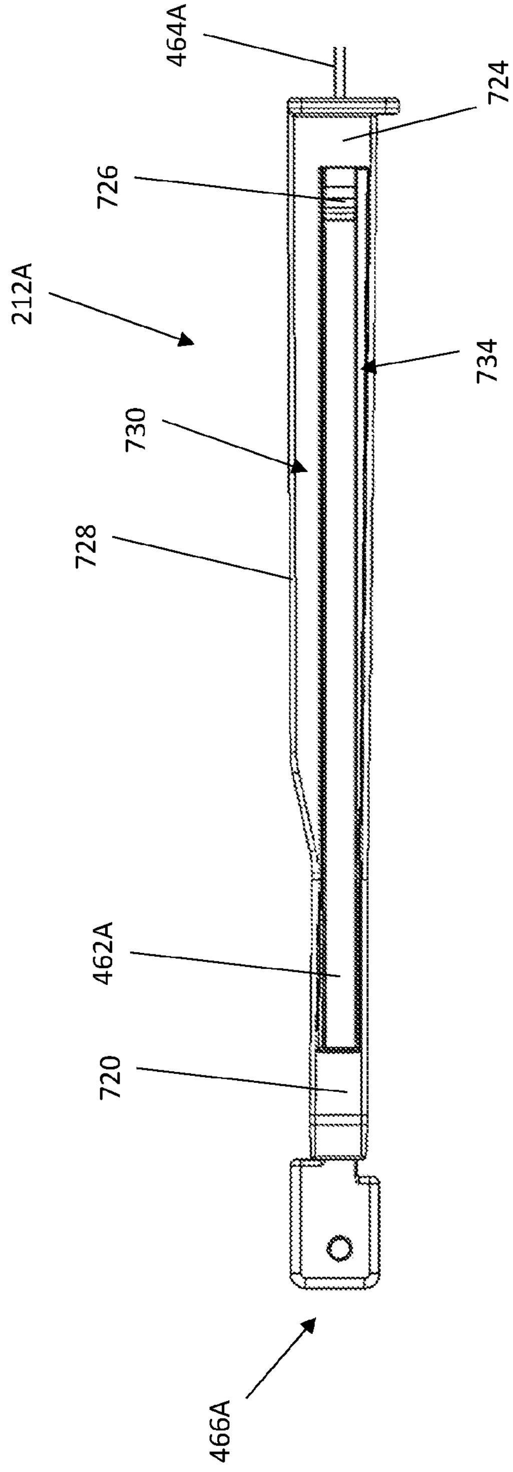
FIG. 30A is a side view of an alternative configuration of an elongate plastic member and a support structure in a minimum length configuration.
Figure 30B:
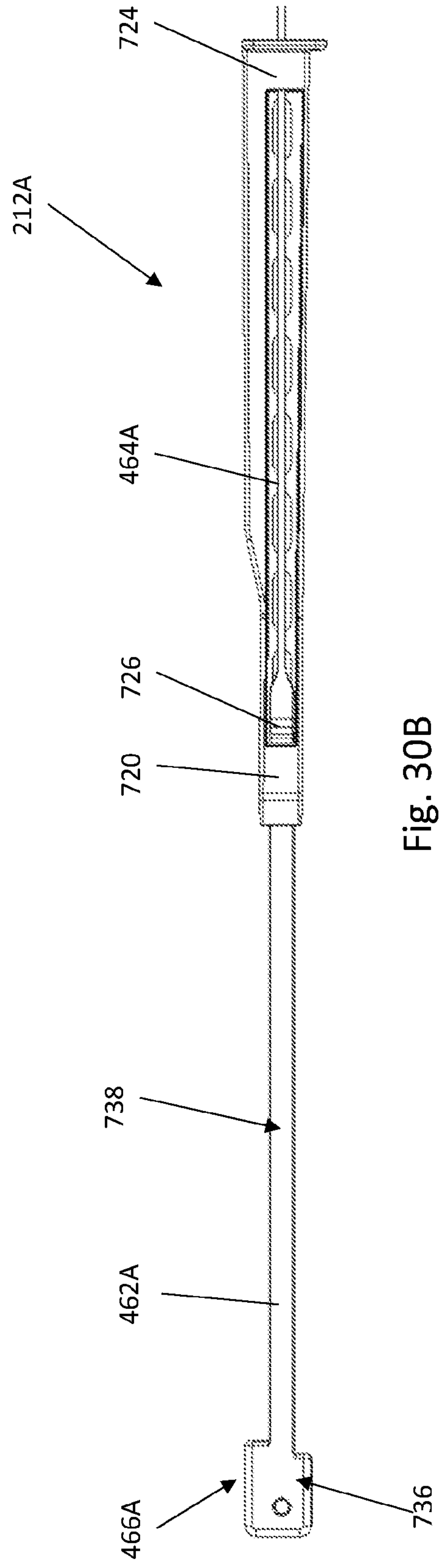
FIG. 30B is a side view of the elongate plastic member and the support structure of FIG. 30A in a maximum length configuration.
Figure 30C:
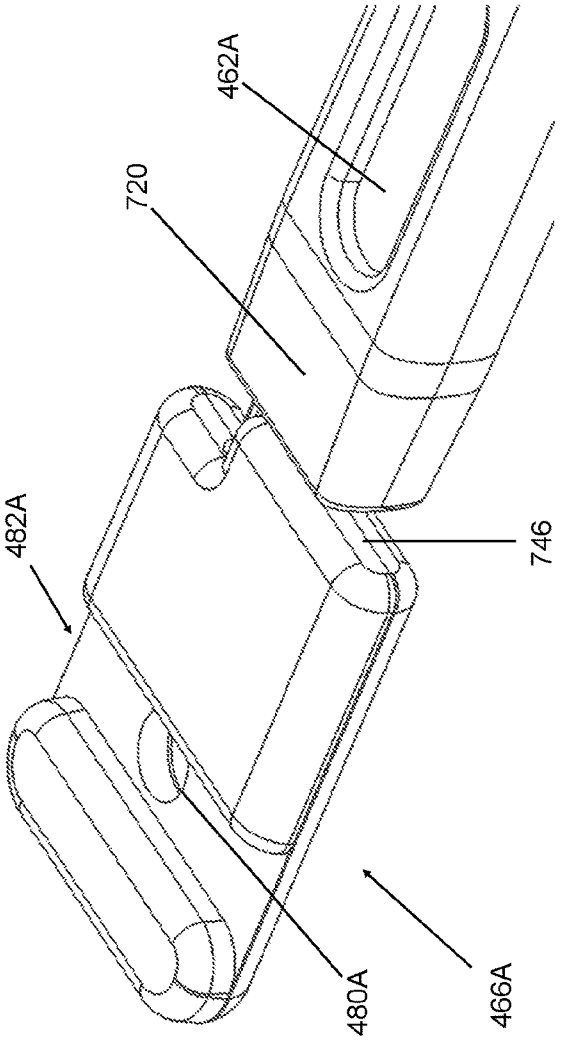
FIG. 30C is a perspective view of a user-contacting side of the elongate plastic member and the support structure of FIG. 30A in the minimum length configuration.
Figure 30D:
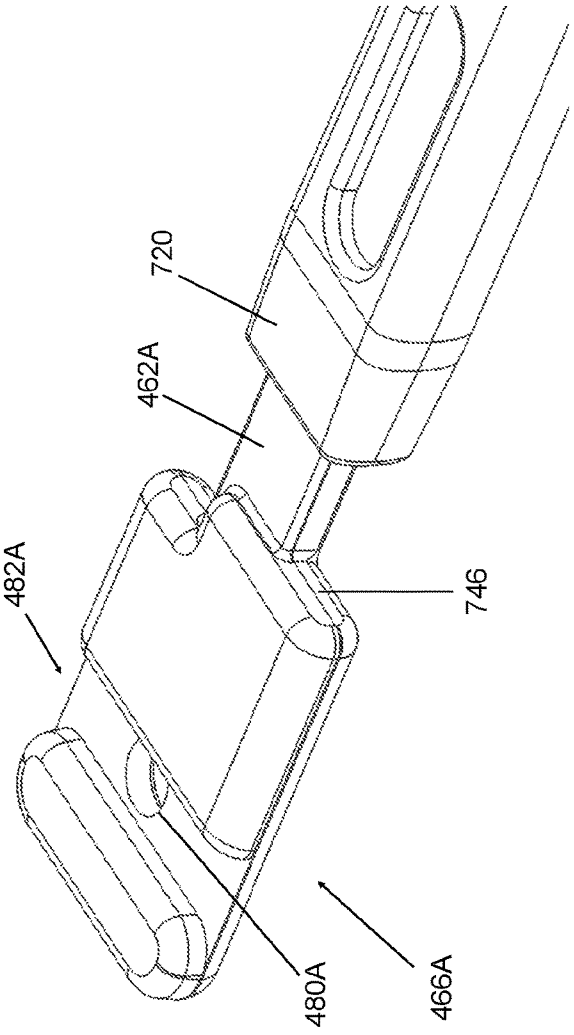
FIG. 30D is a perspective view of the user-contacting side of the elongate plastic member and the support structure of FIG. 30A in a partially extended configuration.
Figure 31:
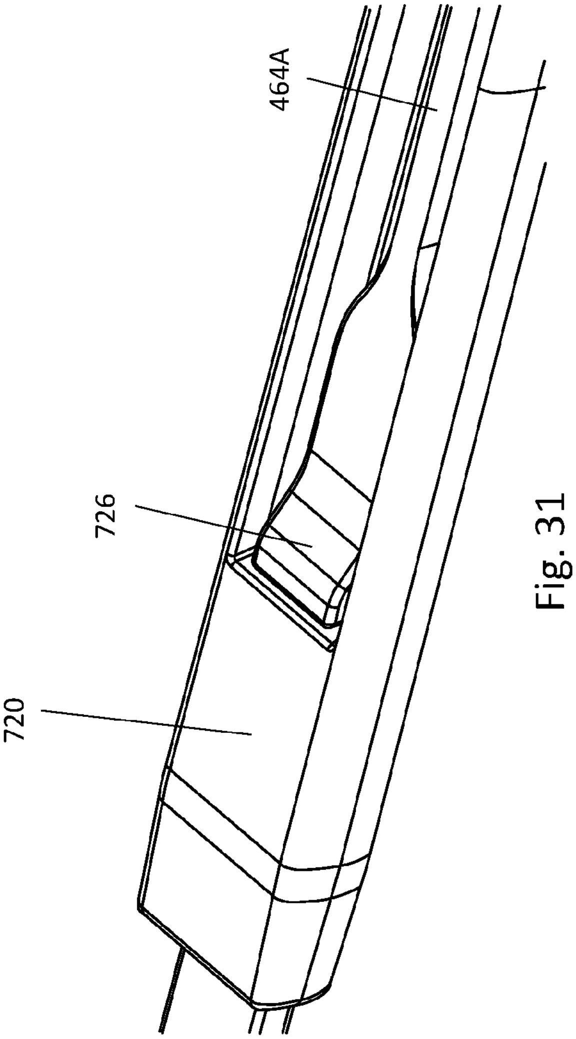
FIG. 31 is an enlarged perspective view of a mechanical hard stop of the elongate plastic member and support of FIG. 30A.
Figure 32:
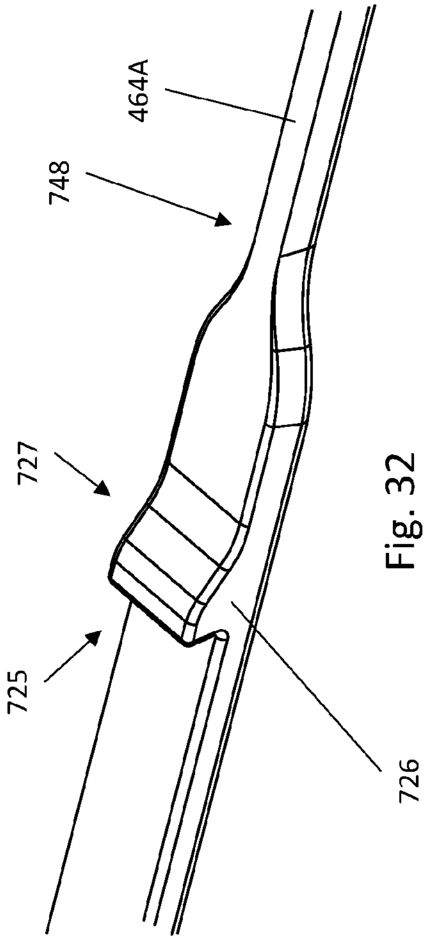
FIG. 32 is an enlarged perspective view of the mechanical hard stop of FIG. 31.

In the illustrated configurations, the elongate plastic member 460A can include a mechanical stop feature 726 configured to engage with the support structure 728. FIGS. 30A and 30C illustrate the side strap 212A in a fully retracted configuration in which the side strap 212A is at a minimum length and/or the lateral collar 720 of the support structure 728 abuts the hub 466A. FIG. 30D illustrates the side strap 212A in a partially extended configuration in which the side strap 212A is at a partially extended length. FIGS. 30B and 31 illustrate the side strap 212A in a fully extended configuration in which the side strap 212A is at a maximum length and/or the mechanical stop feature 726 abuts against the lateral collar 720 of the support structure 728. In some configuration, the mechanical stop feature 726 can be positioned between the first portion 462A and the second portion 464A. The mechanical stop feature 726 can be positioned at or near the transition region 748. In some configurations, the mechanical stop feature 726 can have a rigid formation being a projection, a lug, a bar, or a rib that projects radially outwardly from the elongate plastic member 460A. In the illustrated example, the mechanical stop feature 726 can have a ramped edge 727 and a tooth-like edge 725. During manufacturing, the second portion 464A of the elongate plastic member 460A can be passed through the collars 720, 724 of the support structure 728. The ramped edge 727 can allow the first portion 462A to be passed through the lateral collar 720 as well.

In some configurations, the lateral collar 720 of the support structure 728 can be configured to engage with the elongate plastic member 460A to constrain the elongate plastic member 460A. For example, in the fully retracted configuration shown in FIG. 30A, a lateral wall of the lateral collar 720 can abut the abutment wall 746 (FIG. 29) and the first side 702 of the hub 466A to prevent the elongate plastic member 460A from being further pulled through the directional lock 430 in a retracting direction. This abutment can form a non-elastic limit on the amount by which the elongate plastic member 460A can extend through the directional lock 430. In other words, the limit may not be dependent on any elastic properties of the elastic portion 444 of the cover 440 (FIG. 2). In addition, the side strap 212A can be at its minimum length in this position and the headgear can be at a minimum headgear size. In some configurations, the elongate plastic member 460A can move in an extending direction by overcoming the first resistance of the directional locks 430 until the tooth-like edge 725 of the stop 726 abuts a medial wall of the lateral collar 720, as shown in FIG. 30B. This abutment can limit the amount by which the elongate plastic member 460A can be pulled from the directional lock 430. In addition, the side strap 212A can be at its maximum length in this position and the headgear can be at a maximum headgear size. Examples of elongate members (e.g., filaments), support structures, and mechanical stop features having similar constructions in a general sense and used in similar applications are disclosed in WO2020/096467, the entirety of which is incorporated by reference herein In the illustrated configuration, opposing sides of the lateral collar 720 define minimum and maximum positions of the elongate plastic member 460A (by interaction with the hub 466A and mechanical stop 726). However, other arrangements are possible in which interaction, engagement or physical contact between any suitable surfaces of the elongate plastic member 460A and the support structure 728 defines minimum and maximum positions or extensions. For example, the mechanical stop 726 can be configured to abut the collars 720, 724 when the elongate plastic member 460A is slid through those collars 720, 724 such that the abutment between the collars 720, 724 and the mechanical stop 726 is configured to limit the movement of the elongate plastic member 460A. For example, the mechanical stop 726 can be configured to abut a lateral wall of the medial collar 724 in the fully retracted position to prevent the elongate plastic member 460A from being further pulled through the directional lock 430 in a retracting direction.

CONCLUSION

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Moreover, the following terminology may have been used herein. The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

What is claimed is:

1. A rear portion of a respiratory mask headgear, comprising:

a unitary body portion comprising a plastic material, the body portion comprising:

an upper strap having a first end, a second end, a length between the first end and the second end, and a width;

a lower strap having a first end, a second end, a length between the first end and the second end, and a width; and a junction between the first end of the upper strap and the first end of the lower strap, the junction comprising a base portion and a living hinge between the base portion and one of the upper strap and the lower strap;

wherein the living hinge is defined by a slot that extends through an entirety of a thickness of the body portion and extends into the one of the upper strap and the lower strap from an edge of the one of the upper strap and the lower strap such that the slot defines an open end, wherein a portion of the slot is formed by a rounded protrusion of the base portion of the junction.

2. The rear portion of a respiratory mask headgear of claim 1, wherein the living hinge defines a length that is less than a width of the base portion of the junction and/or the width of the one of the upper strap and the lower strap to which the living hinge is joined, the width of the base portion being a maximum width measured in a direction that extends between an upper edge of the upper strap and a lower edge of the lower strap, and the length of the living hinge being a length of a reduced width portion of the junction measured in a direction along the length of the one of the upper strap and the lower strap to which the living hinge is joined.

3. The rear portion of a respiratory mask headgear of claim 2, wherein the length of the living hinge is less than about two-thirds of the width of the respective upper strap or lower strap to which the living hinge is joined.

4. The rear portion of a respiratory mask headgear of claim 1, wherein the junction is symmetrical about an axis passing through the junction and between the upper strap and the lower strap.

5. The rear portion of a respiratory mask headgear of claim 1, wherein the length of the upper strap is a first length and the length of the lower strap is a second length, wherein the second length is greater than the first length.

6. The rear portion of a respiratory mask headgear of claim 1, wherein the width of the lower strap is greater than the width of the upper strap.

7. The rear portion of a respiratory mask headgear of claim 1, wherein the living hinge is a first living hinge and the junction further comprises a second living hinge, the first living hinge located between the base portion and the upper strap and the second living hinge located between the base portion and the lower strap.

8. The rear portion of a respiratory mask headgear of claim 1, wherein the slot is arcuate in shape.

9. The rear portion of a respiratory mask headgear of claim 1, wherein the slot extends into the edge of the one of the upper strap and the lower strap that is adjacent the other of the upper strap or the lower strap.

10. The rear portion of a respiratory mask headgear of claim 9, wherein each of the upper strap and the lower strap includes a slot.

11. The rear portion of a respiratory mask headgear of claim 10, wherein each of the slots is arcuate in shape and symmetrical about an axis passing through the junction and between the upper strap and the lower strap.

12. The rear portion of a respiratory mask headgear of claim 1, wherein the living hinge is configured to facilitate rotational movement of the one of the upper strap and the lower strap towards or away from the other of the upper strap or the lower strap.

13. The rear portion of a respiratory mask headgear of claim 11, wherein the slots cooperate to form a part-annular shape opening in the body portion.

14. A rear portion of a respiratory mask headgear, comprising:

a unitary body portion comprising a plastic material, the body portion comprising:

an upper strap having a first end, a second end, a length between the first end and the second end, a thickness between opposing side surfaces, and a width between an upper edge and a lower edge;

a lower strap having a first end, a second end, a length between the first end and the second end, a thickness between opposing side surfaces, and a width between an upper edge and a lower edge; and a junction between the first end of the upper strap and the first end of the lower strap, the junction comprising a base portion and a living hinge between the base portion and one of the upper strap and the lower strap;

wherein each of the upper strap and the lower strap comprise a main strap portion having a first thickness and at least one flange portion having a second thickness that is smaller than the first thickness, wherein the main strap portion extends along an entirety of the length of each of the upper strap and the lower strap from the first junction to the second junction, wherein the at least one flange portion extends along at least one-half of the length of each of the upper strap and the lower strap; and wherein the main strap portion defines an entirety of at least one of the upper edge of the upper strap and the lower edge of the lower strap.

15. The rear portion of a respiratory mask headgear of claim 14, wherein the at least one flange portion extends along only a portion of the length of each of the upper strap and the lower strap.

16. The rear portion of a respiratory mask headgear of claim 14, wherein the main strap portion or the main strap portion and the flange define an entirety of the width of each of the upper strap and the lower strap at any location along the length of a respective one of the upper strap and the lower strap.

17. The rear portion of a respiratory mask headgear of claim 14, wherein the main strap portion defines an entirety of the width of a central portion of each of the upper strap and the lower strap.

18. The rear portion of a respiratory mask headgear of claim 14, wherein the at least one flange portion comprises a first flange portion and a second flange portion located on opposing sides of a central portion of each of the upper strap and the lower strap.

19. The rear portion of a respiratory mask headgear of claim 18, wherein each of the first flange portion and the second flange portion is configured to extend along a respective side of a user's head in use.

20. The rear portion of a respiratory mask headgear of claim 17, wherein the central portion of the upper strap defines a length that is less than a length of the central portion of the lower strap.

21. The rear portion of a respiratory mask headgear of claim 14, wherein the main strap portion defines the entirety of each of the upper edge of the upper strap and the lower edge of the lower strap.

22. The rear portion of a respiratory mask headgear of claim 21, wherein the at least one flange defines a portion of the lower edge of the upper strap and a portion of the upper edge of the lower strap.

23. A rear portion of a respiratory mask headgear, comprising:

a unitary body portion comprising a plastic material, the body portion comprising:

an upper strap having a first end, a second end, a length between the first end and the second end, and a width;

a lower strap having a first end, a second end, a length between the first end and the second end, and a width; and a junction between the first end of the upper strap and the first end of the lower strap, the junction comprising a base portion and a living hinge between the base portion and each of the upper strap and the lower strap;

wherein the living hinge is defined by a slot that extends into an edge of each one of the upper strap and the lower strap that is adjacent the other of the upper strap or the lower strap;

wherein each of the slots is arcuate in shape and symmetrical about an axis passing through the junction and between the upper strap and the lower strap; and wherein a portion of each of the slots is formed by a rounded protrusion of the base portion of the junction.

* * * * *